United States Patent [19]
Chiu

[11] Patent Number: 5,925,528
[45] Date of Patent: Jul. 20, 1999

[54] MURINE CELL LINES WHICH OVER PRODUCE ACIDIC FIBROBLAST GROWTH FACTOR (AFGF) AND METHOD OF USING SAME

[75] Inventor: Ing Ming Chiu, Dublin, Ohio

[73] Assignee: Ohio State University Research Foundation, Columbus, Ohio

[21] Appl. No.: 08/885,418

[22] Filed: Jun. 30, 1997

Related U.S. Application Data

[62] Division of application No. 08/070,165, May 28, 1993, Pat. No. 5,750,365.

[51] Int. Cl.$^6$ ...................................................... C12N 5/10
[52] U.S. Cl. .............................. 435/7.1; 435/6; 435/7.2; 435/365
[58] Field of Search ................................ 438/6, 7.2, 365; 435/7.1

[56] References Cited

U.S. PATENT DOCUMENTS 4,683,195  7/1987  Mullis et al. ................................ 435/6

OTHER PUBLICATIONS

Chiu et al., 1990, Brain–derived Heparin–binding Growth Factors and their Oncogenic Homologs, Tropic Factors and the Nervous System, ed. L.A. Horrocks et al., Raven Press Ltd. New York, pp. 57–74.
Gospodarowicz et al. Comparison of the Ability of Basic and Acidic Fibroblast Growth Factor to Stimulate the Proliferation of an Established Keratinocyte Cell Line. J. Cellu. Physiol. 142:325–333, Feb. 1990.
Basilico et al., 1992, The FGF family of growth factors and oncogenes. *Adv. Cancer Res.* 59:115–165.
Jaye et al., 1986, Human endothelial cell growth factor: cloning, nucleotide sequence, and chromosomal localization. *Science* 23:541–545.
Wang et al., 1989, Cloning of the gene coding for human class I heparin–binding growth factor and its expression in fetal tissue. *Mol. Cell. Biol.* 9:2387–2395.
Abraham et al., 1986, Human basic fibroblast growth factor: nucleotide sequence and genomic organization. *EMBO J.* 5:2523–2528.
Dickson et al., 1987, Potential oncogene product related to growth factors. *Nature* 326–833.
Acland et al., 1990, Subcellular fate of int–2 oncoprotein is determined by choice of initiation codon. *Nature* 343:662–665.
Delli–Bovi et al., 1987, An oncogene isolated by transfection of Kaposi's sarcoma DNA encodes a growth factor that is a member of the FGF family. *Cell* 50:729–737.
Taira et al., 1987, cDNa sequence of human transforming gene hst and identification of the coding sequence required for transforming activity. *Proc. Natl. Acad. Sci. USA* 84:2980–2984.
Zhan et al., 1988, The human FGF–5 oncogene encodes a novel protein related to fibroblast growth factors. *Mol. Cell. Biol.* 8:3487–3495.

deLapeyriere et al, 1990, Structure, chromosome mapping, and expression of the murine FGF–6 gene. *Oncogene* 5:823–831.
Finch et al., 1989, Human KGF is FGF–related with properties of a paracrine effector of epithelial cell growth. *Science* 245:752–755.
Tanaka et al., 1992, Cloning and characterization of an androgen–induced growth factor essential for the androgen–dependent growth of mouse mammary carcinoma cells. *Proc. Natl. Acad. Sci. USA* 89:8928–8932.
Werner et al., 1992, Large induction of keratinocyte growth factor expression in the dermis during wound healing. *Proc. Natl. Acad. Sci. USA* 89:6896–6900.
Johnson et al., 1993, Structural and functional diversity in the FGF receptor multigene family, *Adv. Cancer Res.* 60:1–41.
Ruta et al., 1989, Receptor for acidic fibroblast growth factor is related to the tyrosine kinase encoded by the fms–like gene (FLG). *Proc. Natl. Acad. Sci. USA* 86:8722–8726.
Dionne et al., 1990, Cloning and expression of two distinct high–affinity receptors cross–reacting with acidic and basic fibroblast growth factor. *EMBO J.* 9:2685–2692.
Johnson et al., 1990, Diverse forms of a receptor for acidic and basic fibroblast growth factors. *Mol. Cell. Biol.* 10:4728–4736.
Kornbluth et al., 1988, Novel tyrosine kinase identified by phosphotyronsine antibody screening of cDNA libraries. *Mol. Cell. Biol.* 8:5541–5544.
Keegan et al., 1991, Isolation of an additional member of the fibroblast growth factor receptor family, FGFR–3. *Proc. Natl. Acad. Sci. USA* 88:1095–1099.
Partanen et al., 1991, FGFR–4, a novel acidic fibroblast growth factor receptor with a distinct expression pattern. *EMBO J.* 10:1347–1354.
Williams et al., 1988, The immunoglobulin superfamily–domains for cell surface recognition. *Ann. Rev. Immunol.* 6:381–405.
Mansukhani et al., 1990, A murine fibroblast growth factor (FGF) receptor expressed in CHO cells is activated by basic FGF and Kaposi FGF. *Proc. Natl. Acad. Sci. USA* 87:4378–4382.

(List continued on next page.)

*Primary Examiner*—John Ulm
*Attorney, Agent, or Firm*—Emch, Schaffer, Schaub & Porcello, Co., Inc.

[57] ABSTRACT

The present invention thus relates to novel newt aFGF cDNA and sequence, newt FGFR1 cDNA and sequence, newt FGFR2 cDNA and sequence, newt FGFR3 cDNA and sequence, newt KGFR cDNA and sequence, and CHO-K1 cell line (KPTr2—2) expressing newt KGFR. Mutant cell lines (Tr31-5-1 and Tr33-1-2) that become non-responsive to aFGF stimulation are used to differentiate biological activities among different forms of aFGF and other FGF proteins. These novel sequences and cell lines substantially enhance the availability of newt acidic fibroblast growth factor and are useful for producing compositions for promoting growth and/or wound healing

6 Claims, 14 Drawing Sheets

OTHER PUBLICATIONS

Fujita et al., 1991, The expression of two isoforms of the human fibroblast growth factor receptor (flg) is directed by alternative splicing. *Biochem. Biophys. Res. Comm.* 174:946–951.

Champion–Arnaud et al, 1991, Multiple mRNAs code for proteins related to the BEK fibroblast growth factor receptor. *Oncogene* 6:979–987.

Eisemann et al., 1991, Alternative splicing generates at least five different isoforms of the human basic–FGF receptor. *Oncogene* 6:1195–1202.

Johnson et al., 1991, The human fibroblast growth factor receptor genes: A common structural arrangement underlies the mechanisms for generating receptor forms that differ in their third immunoglobulin domain. *Mol. Cell. Biol.* 11:4627–4634.

Yayon et al, 1992, A confined variable region confers ligand specificity on fibroblast growth factor receptors: Implications for the origin of the immunoglobulin fold. *EMBO J.* 11:1885–1890.

Miki et al., 1991, Expression cDNA closing of the KGF receptor by creation of a transforming autocrine loop. *Science* 251:72–75.

Miki et al., 1992, Determination of ligand–binding specificity by alternative splicing: Two distinct growth factor receptors encoded by a single gene. *Proc. Natl. Acad. Sci. USA* 89:246–250.

Mansukhani et al, 1992, Characterization of the murine BEK fibroblast growth factor (FGF) receptor: Activation by three members of the FGF family and requirement for heparin. *Proc. Natl. Acad. Sci. USA* 89:3305–3309.

Whitman et al., 1989, Growth factors in early embryogenesis. *Annu. Rev. Cell. Biol.* 5:93–117.

Hebert et al., 1990, Isolation of cDNAs encoding four mouse FGF family members and characterization of their expression patterns during embryogenesis. *Dev. Biol.* 138:454–463.

Niswander et al., 1992, FGF–4 expression during gastrulation, myogenesis, limb and tooth development in the mouse. *Development* 114:755–768.

Tannahill et al., 1992, Development expression ofthe Xenopus int–2(FGF–3) gene: Activation by mesodermal and neural induction. *Development* 115:696–702.

Mescher et al., 1979, Mitogenic effect of a growth factor derived from myelin on denervated regenerates of newt forelimbs. *J. Exp. Zool.* 207:497–503.

Gospodarowicz et al., 1980, Fibroblast growth factor and the control of vertebrate regeneration and repair. *Ann. N.Y. Acad. Sci.* 339:151–174.

Boilly et al., 1991, Acidic fibroblast growth factor is present in regenerating limb blastemas of axolotls and binds specifically to blastema tissue. *Dev. Biol.* 145:302–310.

Orr–Urteger et al., 1991, Developmental expression of two murine fibroblast growth factor receptors, flg and bek. *Development* 113:1419–1434.

Peters et al, 1992, Two FGF receptor genes are differentially expressed in epithelial and mesenchymal tissues during limb formation and organogenesis in the mouse. *Development* 114:233–243.

Bunnag et al., 1991, Transformed phenotype confered to NIH/3T3 cells by ectopic expressionof heparin–binding growth factor 1/acidic fibroblast growth factor. *In Vitro Cell. Dev. Biol.* 27A:89–96.

Chiu et al. 1990, Alternative splicing generates two forms of mRNA coding for human heparin–binding growth factor 1. *Oncogene* 5:755–762.

Wozney, 1990, *Methods in Enzymol* 182:738–749.

Krust et al., 1986, *EMBO J.* 5:891–897.

Jospodarowicz, 1987, *Methods in Enzymol* 147:106–119.

Jospodarowicz, 1987, *Erdocrine Rev.* 8:95–114.

Jimenez–Gallejo et al., 1985, *Science* 230:1385–1388.

Gautsch–Sova et al., 1986, *Biochem Biophys. Res. Comm.* 140:874–880.

NewtKGFR    ArgSerGlyIleAsnSerSerAsn------AlaGluValThrLeuHisAsnValThrGluAlaAspAla
            :::                           :::                :::
Newtbek     AlaAlaGlyValAlaAsnThrThrAspLysGluIleGlyValLeuValLeuTyrValArgAsnValSerPheGluAspAla GlyGlnTyrThrCysLysValSerAsnTyrIleGlyGluAlaAsnGlnSerAlaTrpThrValLeuProAlaSerGluLys
            :::  :::                              :::
            GlyGluTyrThrCysLeuAlaGlyAsnSerThrGlyIleSerTyrHisThrAlaTrpLeuThrValLeuPro

B

NewtKGFR    ArgSerGlyIleAsnSerSerAsnAlaGluValThrLeuHisAsnValThrGluAlaAspAla
            :::::::::::::::::: :::                     :::  :::
HumanKGFR   HisSerGlyIleAsnSerSerAsnAlaGluValAlaLeuPheAsnValAlaAspAlaAspAlaGlyGlu TyrThrCysLysValSerAsnTyrIleGlyGluAlaAsnGlnSerAlaTrpThrValLeuProAlaSerGluLys
            :::                              :::                        :::
            TyrIleCysLysValSerAsnTyrIleGlyGlnAlaAsnGlnSerAlaTrpThrLeuValProLysGlnGln

C

Newtbek     AlaAlaGlyValAlaAsnThrThrAspLysGluIleGlyValLeuValLeuTyrValArgAsnValSerPheGluAspAla
            :::::::::::::::::::::::::::::::: :::                     :::
Humanbek    AlaAlaGlyValAlaAsnThrThrAspLysGluIleGlyValLeuValLeuTyrIleArgAsnValThrPheGluAspAla GlyGluTyrThrCysLeuAlaGlyAsnSerThrGlyIleSerTyrHisThrAlaTrpLeuThrValLeuPro
            :::                              :::
            GlyGluTyrThrCysLeuAlaGlyAsnSerIleGlyIleSerPheHisSerAlaTrpLeuThrValLeuPro

FIG. 3

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 261 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Notophthalmus viridescens
      (D) DEVELOPMENTAL STAGE: Adult
      (F) TISSUE TYPE: Brain (vii) IMMEDIATE SOURCE:
      (B) CLONE: MP 75-1

(viii) POSITION IN GENOME:
      (C) UNITS: bp (ix) FEATURE:
      (A) NAME/KEY: CDS
      (B) LOCATION: 1..261

(x) PUBLICATION INFORMATION:
      (A) AUTHORS: Patrie, Kevin M
         Botelho, Mary Jane
         Ray, Subir K
         Mehta, Veela B
         Chiu, Ing-Ming
      (C) JOURNAL: J. Biol. Chem.
      (K) RELEVANT RESIDUES IN SEQ ID NO:1: FROM 1 TO 261

(xi) SEQUENCE DESCRIPTION: SEQ ID NO:1:

```
CTT CCC AAT GGA AAC TAC CAG AAG CCT AAG CTC CTG TAC TGC AGC AAC       48
Leu Pro Asn Gly Asn Tyr Gln Lys Pro Lys Leu Leu Tyr Cys Ser Asn
 1               5                  10                  15
```

```
GGA GGG TAC TTC CTG CGA ATA CTC CCA GAT GGC AAG GTG GAC GGG ACA        96
Gly Gly Tyr Phe Leu Arg Ile Leu Pro Asp Gly Lys Val Asp Gly Thr
            20                  25                  30

AGA GAC CGG AGT GAC CCA TAC ATC CAG CTG CAG TTT TAT GCA GAA AGC       144
Arg Asp Arg Ser Asp Pro Tyr Ile Gln Leu Gln Phe Tyr Ala Glu Ser
        35                  40                  45

GTG GGC GAG GTA TAC ATC AAG AGT CTG GAG ACA GGC CAG TAC TTG GCG       192
Val Gly Glu Val Tyr Ile Lys Ser Leu Glu Thr Gly Gln Tyr Leu Ala
    50                  55                  60

ATG GAC AGC GAC GGG CAG TTA TAC GCA TCT CAA TCA CCA AGC GAG GAA       240
Met Asp Ser Asp Gly Gln Leu Tyr Ala Ser Gln Ser Pro Ser Glu Glu
65                  70                  75                  80

TGC CTG TTC TTG GAG CGA CTG                                           261
Cys Leu Phe Leu Glu Arg Leu
                85

(2) INFORMATION FOR SEQ ID NO:2:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO:2:

Leu Pro Asn Gly Asn Tyr Gln Lys Pro Lys Leu Leu Tyr Cys Ser Asn
 1               5                  10                  15

Gly Gly Tyr Phe Leu Arg Ile Leu Pro Asp Gly Lys Val Asp Gly Thr
            20                  25                  30

Arg Asp Arg Ser Asp Pro Tyr Ile Gln Leu Gln Phe Tyr Ala Glu Ser
        35                  40                  45

Val Gly Glu Val Tyr Ile Lys Ser Leu Glu Thr Gly Gln Tyr Leu Ala
    50                  55                  60

Met Asp Ser Asp Gly Gln Leu Tyr Ala Ser Gln Ser Pro Ser Glu Glu
65                  70                  75                  80

Cys Leu Phe Leu Glu Arg Leu
                85

(2) INFORMATION FOR SEQ ID NO:3:

(i) SEQUENCE CHARACTERISTICS:
        (A) LENGTH: 1875 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Notophthalmus viridescens
        (D) DEVELOPMENTAL STAGE: Adult
        (F) TISSUE TYPE: Regenerating forelimb blastema
        (G) CELL TYPE: Mesenchyme and Epithelium (vii) IMMEDIATE SOURCE:
        (A) LIBRARY: lambda gt11
        (B) CLONE: MP10-1

(viii) POSITION IN GENOME:
        (C) UNITS: bp (ix) FEATURE:
        (A) NAME/KEY: CDS
```

(B) LOCATION: 1..1164

(ix) FEATURE:
    (A) NAME/KEY: 3'UTR
    (B) LOCATION: 1165..1875

(x) PUBLICATION INFORMATION:
    (A) AUTHORS: Poulin, Matthew L
    (K) RELEVANT RESIDUES IN SEQ ID NO:3: FROM 1 TO 1874

(xi) SEQUENCE DESCRIPTION: SEQ ID NO:3:

```
GCC AGC TCT TCC ATG AGC TCT GGC GTT ATG CTG GTA CGG CCG TCG CGA        48
Ala Ser Ser Ser Met Ser Ser Gly Val Met Leu Val Arg Pro Ser Arg
 1               5                  10                  15

CTA TCG TCC AGT GGA AGC CCA ATG TTG ACT GGA GTC TCG GAG TAT GAA        96
Leu Ser Ser Ser Gly Ser Pro Met Leu Thr Gly Val Ser Glu Tyr Glu
            20                  25                  30

CTG CCA GAA GAT CCT CGC TGG GAG TTC TCA CGA GAC AGG TTA ATA TTG       144
Leu Pro Glu Asp Pro Arg Trp Glu Phe Ser Arg Asp Arg Leu Ile Leu
        35                  40                  45

GGC AAG CCT CTC GGA GAG GGC TGC TTT GGT CAG GTT GTA ATG GGA GAA       192
Gly Lys Pro Leu Gly Glu Gly Cys Phe Gly Gln Val Val Met Gly Glu
 50                  55                  60

GCA ATT GGC TTG GAC AAG GAG AAA CCC AAC CGA GTG ACT AAA GTA GCA       240
Ala Ile Gly Leu Asp Lys Glu Lys Pro Asn Arg Val Thr Lys Val Ala
             65                  70                  75                  80

GTG AAG ATG TTA AAA TCT GAC GCA ACT GAA AAG GAT TTG TCA GAT CTT       288
Val Lys Met Leu Lys Ser Asp Ala Thr Glu Lys Asp Leu Ser Asp Leu
                 85                  90                  95

ATT TCT GAG ATG GAA ATG ATG AAA ATG ATT GGA AAG CAC AAA AAC ATC       336
Ile Ser Glu Met Glu Met Met Lys Met Ile Gly Lys His Lys Asn Ile
                100                 105                 110

ATC AAT CTT CTT GGT GCA TGT ACG CAG GAT GGC CCA CTG TAT GTC ATT       384
Ile Asn Leu Leu Gly Ala Cys Thr Gln Asp Gly Pro Leu Tyr Val Ile
            115                 120                 125

GTG GAG TAC GCC TCA AAA GGT AAT CTG CGA GAA TAC TTG CGT GCC AGA       432
Val Glu Tyr Ala Ser Lys Gly Asn Leu Arg Glu Tyr Leu Arg Ala Arg
        130                 135                 140

CGT CCT CCG GGC ATG GAG TAC TGT TAT AAT CCC ATC CAT GCT TCC AAG       480
Arg Pro Pro Gly Met Glu Tyr Cys Tyr Asn Pro Ile His Ala Ser Lys
145                 150                 155                 160

GAC ATG CTG TCT TTT AAG GAC CTG GTG TCA TGT GCT TAC CAA GTA GCC       528
Asp Met Leu Ser Phe Lys Asp Leu Val Ser Cys Ala Tyr Gln Val Ala
                165                 170                 175

CGA GGA ATG GAG TAT CTT GCT TCT AAG AAG TGC ATC CAC CGT GAC CTT       576
Arg Gly Met Glu Tyr Leu Ala Ser Lys Lys Cys Ile His Arg Asp Leu
                180                 185                 190

GCA GCT CGA AAC GTG TTA GTA ACG GAA GAC AAT GTC ATG AAG ATT GCA       624
Ala Ala Arg Asn Val Leu Val Thr Glu Asp Asn Val Met Lys Ile Ala
            195                 200                 205

GAC TTT GGC TTG GCG CGA GAT ATC CAT CAC ATC GAT TAT TAC AAG AAG       672
Asp Phe Gly Leu Ala Arg Asp Ile His His Ile Asp Tyr Tyr Lys Lys
        210                 215                 220

ACG ACA AAT GGA CGA TTA CCG GTG AAG TGG ATG GCC CCT GAG GCA CTC       720
Thr Thr Asn Gly Arg Leu Pro Val Lys Trp Met Ala Pro Glu Ala Leu
225                 230                 235                 240

TTT GAC CGC ATA TAT ACT CAT CAA AGT GAC GTC TGG TCT TTC GGC GTG       768
Phe Asp Arg Ile Tyr Thr His Gln Ser Asp Val Trp Ser Phe Gly Val
                245                 250                 255

CTG CTG TGG GAG ATC TTC ACA CTG GGT GGC TCT CCT TAC CCT GGG GTG       816
Leu Leu Trp Glu Ile Phe Thr Leu Gly Gly Ser Pro Tyr Pro Gly Val
                260                 265                 270
```

```
CCA GTC GAA GAA CTC TTC AAG TTG TTA AAA GAG GGG CAC AGA ATG GAC      864
Pro Val Glu Glu Leu Phe Lys Leu Leu Lys Glu Gly His Arg Met Asp
        275                 280                 285

AAA CCC GGC AAC TGC ACA AAT GAA CTA TAC ATG ATG ATG AGA GAC TGC      912
Lys Pro Gly Asn Cys Thr Asn Glu Leu Tyr Met Met Met Arg Asp Cys
        290                 295                 300

TGG CAT GCA GTT CCA TCC CAA AGA CCA ACC TTC AAG CAG CTG GTT GAA      960
Trp His Ala Val Pro Ser Gln Arg Pro Thr Phe Lys Gln Leu Val Glu
305                 310                 315                 320

GAT TTG GAC CGA ATT GTA GCA ATG ACC TCA AAT CAG GAA TAT TTG GAT     1008
Asp Leu Asp Arg Ile Val Ala Met Thr Ser Asn Gln Glu Tyr Leu Asp
        325                 330                 335

CTG TCC ATG CCA ATG GAT CAG TAT TCT CCA GGT TTT CCA GAC ACA CGC     1056
Leu Ser Met Pro Met Asp Gln Tyr Ser Pro Gly Phe Pro Asp Thr Arg
        340                 345                 350

AGT TCT ACG TGT TCC TCA GGA GAG GAC TCT GTG TTC TCC CAT GAT CCT     1104
Ser Ser Thr Cys Ser Ser Gly Glu Asp Ser Val Phe Ser His Asp Pro
        355                 360                 365

TTT CCA GAT GAA CCT TGT CTT CCC AAG TAT CAA CAT GCC AAT GGT GGC     1152
Phe Pro Asp Glu Pro Cys Leu Pro Lys Tyr Gln His Ala Asn Gly Gly
        370                 375                 380

CTT AAA AAA CGC TGACAGACAT GACTTCCAGG CAACAGAAAC TGTGACCTCA         1204
Leu Lys Lys Arg
385

TTTCTACCAT CTAGCCTCTT GGTTTTTATT TTGGGAGGGC AATGTTGTCC AGCCATTAAA   1264

TTACCAGGAA ATGTCTTATT TTTTTATTAT GGACCATAAC ATGCGCCATT ATAGCATCTC   1324

ACTAAGACCA ACACCACCAG CCCATGCAGC ATGCCAGTTT AACAAGCCTT TATCTTGTAT   1384

CACATTGAGT TATGTTTTTT TTAACTTGAA CATTTTACTT ATATTTTGGT CAATGTACTC   1444

GTCAAGTAGG CAGACCATAA AGTCCCTGGG AACAGTCTGC TATCTGGGAC CTTGATAGGA   1504

AAAAGTGAAG CAGTCTAACC TCTGTGGCTT CTTGAGATAC ATTTAAGACC AGAATGCCCT   1564

CCGGTACTTT TCAAAAGAAA TAAAGAACAG TTGATCCATC GCAACACAGA GTACGAGAAA   1624

TACACACCTT GGAGAATAAA GGGATGCAGA TAGTCTACCC GCTTGCAGTT CCATTCATGC   1684

TGAGAGCAGT ATCTACTCAT GGAAATTGGA TGAGCCTATC TGGGGGAGTT CTAATGAGCC   1744

TGAACCCTCT TTTGTTTTGG ATTTTGGAAA CTTGGATCAC CCTTCAGTTC TAGAAGGCCT   1804

CTTGGACACA GCAACTTATG ATTGGCTCTT CTCTTTAGGG ATGATTGAAG CTTCCTTGCC   1864

AGTCGTTGTG G                                                        1875

(2) INFORMATION FOR SEQ ID NO:4:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO:4:

Ala Ser Ser Met Ser Ser Gly Val Met Leu Val Arg Pro Ser Arg
 1               5                  10                  15

Leu Ser Ser Gly Ser Pro Met Leu Thr Gly Val Ser Glu Tyr Glu
                20                  25                  30

Leu Pro Glu Asp Pro Arg Trp Glu Phe Ser Arg Asp Arg Leu Ile Leu
            35                  40                  45

Gly Lys Pro Leu Gly Glu Gly Cys Phe Gly Gln Val Val Met Gly Glu
        50                  55                  60
```

```
Ala Ile Gly Leu Asp Lys Glu Lys Pro Asn Arg Val Thr Lys Val Ala
 65                  70                  75                  80

Val Lys Met Leu Lys Ser Asp Ala Thr Glu Lys Asp Leu Ser Asp Leu
                 85                  90                  95

Ile Ser Glu Met Glu Met Met Lys Met Ile Gly Lys His Lys Asn Ile
            100                 105                 110

Ile Asn Leu Leu Gly Ala Cys Thr Gln Asp Gly Pro Leu Tyr Val Ile
            115                 120                 125

Val Glu Tyr Ala Ser Lys Gly Asn Leu Arg Glu Tyr Leu Arg Ala Arg
        130                 135                 140

Arg Pro Pro Gly Met Glu Tyr Cys Tyr Asn Pro Ile His Ala Ser Lys
145                 150                 155                 160

Asp Met Leu Ser Phe Lys Asp Leu Val Ser Cys Ala Tyr Gln Val Ala
                165                 170                 175

Arg Gly Met Glu Tyr Leu Ala Ser Lys Lys Cys Ile His Arg Asp Leu
            180                 185                 190

Ala Ala Arg Asn Val Leu Val Thr Glu Asp Asn Val Met Lys Ile Ala
        195                 200                 205

Asp Phe Gly Leu Ala Arg Asp Ile His His Ile Asp Tyr Tyr Lys Lys
        210                 215                 220

Thr Thr Asn Gly Arg Leu Pro Val Lys Trp Met Ala Pro Glu Ala Leu
225                 230                 235                 240

Phe Asp Arg Ile Tyr Thr His Gln Ser Asp Val Trp Ser Phe Gly Val
                245                 250                 255

Leu Leu Trp Glu Ile Phe Thr Leu Gly Gly Ser Pro Tyr Pro Gly Val
            260                 265                 270

Pro Val Glu Glu Leu Phe Lys Leu Leu Lys Glu Gly His Arg Met Asp
        275                 280                 285

Lys Pro Gly Asn Cys Thr Asn Glu Leu Tyr Met Met Met Arg Asp Cys
        290                 295                 300

Trp His Ala Val Pro Ser Gln Arg Pro Thr Phe Lys Gln Leu Val Glu
305                 310                 315                 320

Asp Leu Asp Arg Ile Val Ala Met Thr Ser Asn Gln Glu Tyr Leu Asp
                325                 330                 335

Leu Ser Met Pro Met Asp Gln Tyr Ser Pro Gly Phe Pro Asp Thr Arg
            340                 345                 350

Ser Ser Thr Cys Ser Ser Gly Glu Asp Ser Val Phe Ser His Asp Pro
            355                 360                 365

Phe Pro Asp Glu Pro Cys Leu Pro Lys Tyr Gln His Ala Asn Gly Gly
        370                 375                 380

Leu Lys Lys Arg
385

(2) INFORMATION FOR SEQ ID NO:5:

(i) SEQUENCE CHARACTERISTICS:
        (A) LENGTH: 2675 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Notophthalmus viridescens
```

```
          (D) DEVELOPMENTAL STAGE: Adult
          (F) TISSUE TYPE: Regenerating forelimb blastema
          (G) CELL TYPE: Mesenchyme and Epithelium (vii) IMMEDIATE SOURCE:
          (A) LIBRARY: lambda gt11
          (B) CLONE: KP23-1

(viii) POSITION IN GENOME:
          (C) UNITS: bp (ix) FEATURE:
          (A) NAME/KEY: 5'UTR
          (B) LOCATION: 1..324

(ix) FEATURE:
          (A) NAME/KEY: CDS
          (B) LOCATION: 325..2511

(ix) FEATURE:
          (A) NAME/KEY: 3'UTR
          (B) LOCATION: 2512..2675

(x) PUBLICATION INFORMATION:
          (A) AUTHORS: Poulin, Matthew L
          (B) TITLE: Nucleotide sequences of two newt
              (Notophthalmus viridescens) fibroblast growth
               factor receptor-2 variants
          (C) JOURNAL: Biochim. Biophys. Acta
          (D) VOLUME: 1220
          (F) PAGES: 209-211
          (G) DATE: 1994
          (K) RELEVANT RESIDUES IN SEQ ID NO:5: FROM 1 TO 2675

(xi) SEQUENCE DESCRIPTION: SEQ ID NO:5:

GAATTCCCGA CTGTTTCCCA CGGAATAGGC TCTTGGATTA GCAGTATTTT CCCTTCCTAC      60

CAGTTTTGGG GGGTGTCGGT CGCACCCCCC ACCTAGCTCT GGATAGAAGC ACGTCCTGTA     120

CCTCGGCCGC CCCAGAGCTG GGGGCCTGCG CCGGTCTTCG CCCCCCTGGC TTCTCTCCAC     180

GCCAGAGGTG GTGCACGCTT CAGAAGGTCT CTGATTTGTG GCGGTGAAGA CCCTGGTTGC     240

AGCTCATGCT GGCGCAGAGG CCTTCTGATG GGAAGAAAGT CCACATGGCG ATGCAGGGCA     300

GGACCGGGGC GTGGCATTGA GAGG ATG TTC AGC TGG AGT TAT CTT ATG GGC        351
                           Met Phe Ser Trp Ser Tyr Leu Met Gly
                             1               5

CTG GTC ATG GTT GCC ACG GCA ACA CTT TCT CTA GCA AGG CCA TCG TAC        399
Leu Val Met Val Ala Thr Ala Thr Leu Ser Leu Ala Arg Pro Ser Tyr
 10              15                  20                  25

AAC ATT GCA GAA GAT ACT ACA CTG GAA CCA GAA GAT GCA AAC TCA TCA        447
Asn Ile Ala Glu Asp Thr Thr Leu Glu Pro Glu Asp Ala Asn Ser Ser
             30                  35                  40

GGG GAT GAT GAA GAC GAC AAC GAC GGC TCG GAA GAT TTC ACA AAT GAC        495
Gly Asp Asp Glu Asp Asp Asn Asp Gly Ser Glu Asp Phe Thr Asn Asp
         45                  50                  55

AAC AAC CAC ATG AGG GCT CCG TAC TGG ACG AAT ACA GAA AAA TTG GAA        543
Asn Asn His Met Arg Ala Pro Tyr Trp Thr Asn Thr Glu Lys Leu Glu
     60                  65                  70

AAG AAA CTC CAT GCT GTG CCC GCT GCC AAC ACT GTG AAG TTC CGC TGT        591
Lys Lys Leu His Ala Val Pro Ala Ala Asn Thr Val Lys Phe Arg Cys
 75                  80                  85

CCA GCC GGT GGC AAC CCT ACG CCC TCC ATG AGG TGG CTG AAG AAC GGC        639
Pro Ala Gly Gly Asn Pro Thr Pro Ser Met Arg Trp Leu Lys Asn Gly
 90                  95                 100                 105

AAG GAG TTC AAG CAG GAG CAC CGC ATT GGC GGC TTC AAG GTA CGT AGT        687
Lys Glu Phe Lys Gln Glu His Arg Ile Gly Gly Phe Lys Val Arg Ser
                 110                 115                 120

CAA CAC TTC AGC CTG ATC ATG GAG AGC GTG GTT CCC TCT GAC GAG GGC        735
Gln His Phe Ser Leu Ile Met Glu Ser Val Val Pro Ser Asp Glu Gly
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     | 125 |     |     |     | 130 |     |     |     | 135 |     |     |     |     |      |
| AAC | TAC | ACC | TGT | ATC | ATG | GAG | AAC | GAG | TAT | GGA | TCC | ATC | AAT | CAC | ACC | 783  |
| Asn | Tyr | Thr | Cys | Ile | Met | Glu | Asn | Glu | Tyr | Gly | Ser | Ile | Asn | His | Thr |      |
|     |     |     |     | 140 |     |     |     | 145 |     |     |     | 150 |     |     |     |      |
| TAC | CAC | CTG | GAT | GTT | GTC | GAG | CGG | TCA | CCC | CAC | CGG | CCA | ATA | CTC | CAA | 831  |
| Tyr | His | Leu | Asp | Val | Val | Glu | Arg | Ser | Pro | His | Arg | Pro | Ile | Leu | Gln |      |
|     | 155 |     |     |     |     | 160 |     |     |     |     | 165 |     |     |     |     |      |
| GCT | GGG | CTT | CCG | GCA | AAC | ACA | ACC | ACA | AAA | GTT | GGG | GGC | GAT | GCA | GAG | 879  |
| Ala | Gly | Leu | Pro | Ala | Asn | Thr | Thr | Thr | Lys | Val | Gly | Gly | Asp | Ala | Glu |      |
| 170 |     |     |     |     | 175 |     |     |     |     | 180 |     |     |     |     | 185 |      |
| TTT | GTT | TGC | AAA | GTC | TAC | AGT | GAC | GCA | CAG | CCA | CAT | ATC | CAA | TGG | ATT | 927  |
| Phe | Val | Cys | Lys | Val | Tyr | Ser | Asp | Ala | Gln | Pro | His | Ile | Gln | Trp | Ile |      |
|     |     |     |     | 190 |     |     |     | 195 |     |     |     | 200 |     |     |     |      |
| CGA | CAT | TTT | GAG | CTG | AAT | GGC | AGT | AAA | ATT | GGA | CCT | GAC | GGG | CAT | CCC | 975  |
| Arg | His | Phe | Glu | Leu | Asn | Gly | Ser | Lys | Ile | Gly | Pro | Asp | Gly | His | Pro |      |
|     |     |     | 205 |     |     |     |     | 210 |     |     |     |     | 215 |     |     |      |
| TAT | CTG | AAA | GTG | CTA | AAG | GCG | GCC | GGT | GTT | AAC | ACC | ACG | GAC | AAA | GAG | 1023 |
| Tyr | Leu | Lys | Val | Leu | Lys | Ala | Ala | Gly | Val | Asn | Thr | Thr | Asp | Lys | Glu |      |
|     |     | 220 |     |     |     |     | 225 |     |     |     |     | 230 |     |     |     |      |
| ATC | GAA | GTC | CTC | TAT | GTG | CGC | AAT | GTC | TCT | TTT | GAG | GAT | GCT | GGG | GAG | 1071 |
| Ile | Glu | Val | Leu | Tyr | Val | Arg | Asn | Val | Ser | Phe | Glu | Asp | Ala | Gly | Glu |      |
| 235 |     |     |     |     | 240 |     |     |     |     | 245 |     |     |     |     |     |      |
| TAT | ACG | TGC | TTG | GCG | GGT | AAT | TCT | ACC | GGG | ATC | TCC | TAT | CAC | ACT | GCA | 1119 |
| Tyr | Thr | Cys | Leu | Ala | Gly | Asn | Ser | Thr | Gly | Ile | Ser | Tyr | His | Thr | Ala |      |
| 250 |     |     |     | 255 |     |     |     |     | 260 |     |     |     |     | 265 |     |      |
| TGG | TTG | ACC | GTT | CTG | CCA | GAT | GAA | GAA | CGG | GAA | CTG | GAT | TCA | TCA | TCG | 1167 |
| Trp | Leu | Thr | Val | Leu | Pro | Asp | Glu | Glu | Arg | Glu | Leu | Asp | Ser | Ser | Ser |      |
|     |     |     |     | 270 |     |     |     | 275 |     |     |     | 280 |     |     |     |      |
| GAG | TAT | ACG | GAA | ATC | GCC | ATC | TAC | TGT | GTG | GGA | GGC | TTC | CTG | ATC | ACC | 1215 |
| Glu | Tyr | Thr | Glu | Ile | Ala | Ile | Tyr | Cys | Val | Gly | Gly | Phe | Leu | Ile | Thr |      |
|     |     |     | 285 |     |     |     |     | 290 |     |     |     |     | 295 |     |     |      |
| TGC | ATG | ATT | GGC | ACA | ATC | ATG | GTG | TGC | CAC | ATG | AAG | GGC | AGA | GGC | AAG | 1263 |
| Cys | Met | Ile | Gly | Thr | Ile | Met | Val | Cys | His | Met | Lys | Gly | Arg | Gly | Lys |      |
|     |     | 300 |     |     |     |     | 305 |     |     |     |     | 310 |     |     |     |      |
| AAG | TCT | GAC | TTC | AGC | AGC | CCA | CCC | GCT | GTG | CAC | AAG | CTG | AGC | AAG | AGT | 1311 |
| Lys | Ser | Asp | Phe | Ser | Ser | Pro | Pro | Ala | Val | His | Lys | Leu | Ser | Lys | Ser |      |
| 315 |     |     |     |     | 320 |     |     |     |     | 325 |     |     |     |     |     |      |
| CTC | CCC | CTG | CGC | AGA | CAG | GTA | ACA | GTG | TCT | GCT | GAC | TCC | AGC | TCT | TCT | 1359 |
| Leu | Pro | Leu | Arg | Arg | Gln | Val | Thr | Val | Ser | Ala | Asp | Ser | Ser | Ser | Ser |      |
| 330 |     |     |     |     | 335 |     |     |     |     | 340 |     |     |     |     | 345 |      |
| ATG | AAC | TCC | AAC | ACT | CCA | CTG | GTC | CGG | ATC | ACC | ACT | CGC | CTG | TCT | TCC | 1407 |
| Met | Asn | Ser | Asn | Thr | Pro | Leu | Val | Arg | Ile | Thr | Thr | Arg | Leu | Ser | Ser |      |
|     |     |     |     | 350 |     |     |     | 355 |     |     |     | 360 |     |     |     |      |
| AAC | AAT | GAC | ACC | CAC | TTG | CTG | GCC | GGG | GTC | TCC | GAG | TAT | GAG | CTG | CCA | 1455 |
| Asn | Asn | Asp | Thr | His | Leu | Leu | Ala | Gly | Val | Ser | Glu | Tyr | Glu | Leu | Pro |      |
|     |     |     | 365 |     |     |     |     | 370 |     |     |     |     | 375 |     |     |      |
| GAG | GAC | CCC | AAG | TGG | GAG | TAT | CCA | AGG | GAA | AAG | CTC | ACG | CTG | GGG | AAG | 1503 |
| Glu | Asp | Pro | Lys | Trp | Glu | Tyr | Pro | Arg | Glu | Lys | Leu | Thr | Leu | Gly | Lys |      |
|     |     | 380 |     |     |     |     | 385 |     |     |     |     | 390 |     |     |     |      |
| CCC | CTG | GGC | GAA | GGC | TGC | TTC | GGG | CAG | GTG | GTG | ATG | GCA | GAG | GCG | GTG | 1551 |
| Pro | Leu | Gly | Glu | Gly | Cys | Phe | Gly | Gln | Val | Val | Met | Ala | Glu | Ala | Val |      |
|     | 395 |     |     |     |     | 400 |     |     |     |     | 405 |     |     |     |     |      |
| GGC | ATC | GAC | AAG | GAC | CGG | CCC | AAA | GAT | GCA | GCG | ACC | GTG | GCA | GTG | AAG | 1599 |
| Gly | Ile | Asp | Lys | Asp | Arg | Pro | Lys | Asp | Ala | Ala | Thr | Val | Ala | Val | Lys |      |
| 410 |     |     |     |     | 415 |     |     |     |     | 420 |     |     |     |     | 425 |      |
| ATG | CTG | AAA | GAC | GAT | GCA | ACC | GAG | AAG | GAT | CTT | TCT | GAT | CTG | GTG | TCT | 1647 |
| Met | Leu | Lys | Asp | Asp | Ala | Thr | Glu | Lys | Asp | Leu | Ser | Asp | Leu | Val | Ser |      |
|     |     |     |     | 430 |     |     |     | 435 |     |     |     | 440 |     |     |     |      |
| GAG | ATG | GAA | ATG | ATG | AAG | ATG | ATT | GGG | AAG | CAT | AAA | AAT | ATC | ATC | AAT | 1695 |
| Glu | Met | Glu | Met | Met | Lys | Met | Ile | Gly | Lys | His | Lys | Asn | Ile | Ile | Asn |      |

```
                    445                     450                     455
CTT CTA GGA GCG TGC ACC CAA GAT GGC CCA CTC TAC GTG ATA GTC GAA       1743
Leu Leu Gly Ala Cys Thr Gln Asp Gly Pro Leu Tyr Val Ile Val Glu
        460                     465                     470

TAT GCC TCC AAG GGG AAC TTG CGT GAA TAC TTG CGC ACC CGC CGC CCA       1791
Tyr Ala Ser Lys Gly Asn Leu Arg Glu Tyr Leu Arg Thr Arg Arg Pro
        475                     480                     485

CCT GGC ATG GAG TAC TCC TTT GAC ATC AAC AGA ATT CCT GAA GAG CAG       1839
Pro Gly Met Glu Tyr Ser Phe Asp Ile Asn Arg Ile Pro Glu Glu Gln
490                     495                     500                 505

ATG ACC TTC AAG GAC CTA GTG TCT GCA ACG TAC CAA CTG GCC AGG GGA       1887
Met Thr Phe Lys Asp Leu Val Ser Cys Thr Tyr Gln Leu Ala Arg Gly
                510                     515                     520

ATG GAG TAC CTG GCA TCA CAG AAG TGC ATC CAT CGG GAC TTG GCA GCT       1935
Met Glu Tyr Leu Ala Ser Gln Lys Cys Ile His Arg Asp Leu Ala Ala
                525                     530                     535

CGG AAT GTC TTG GTG ACG GAA ACC AAC GTC ATG AAA ATT GCA GAT TTT       1983
Arg Asn Val Leu Val Thr Glu Thr Asn Val Met Lys Ile Ala Asp Phe
                540                     545                     550

GGT TTG GCC CGA GAC ATC AAC AAC ATC GAC TAC TAC AAA AAA ACA ACC       2031
Gly Leu Ala Arg Asp Ile Asn Asn Ile Asp Tyr Tyr Lys Lys Thr Thr
555                     560                     565

AAT GGC CGG CTC CCC GTG AAG TGG ATG GCT CCC GAG GCG CTG TTT GAC       2079
Asn Gly Arg Leu Pro Val Lys Trp Met Ala Pro Glu Ala Leu Phe Asp
570                     575                     580                 585

AGA GTC TAC ACA CAT CAG AGT GAC GTC TGG TCT TTC GGT GTG CTT ATG       2127
Arg Val Tyr Thr His Gln Ser Asp Val Trp Ser Phe Gly Val Leu Met
                590                     595                     600

TGG GAG ATC TTC ACA CTG GGG GGT TCC CCA TAC CCT GGA ATT CCA GTT       2175
Trp Glu Ile Phe Thr Leu Gly Gly Ser Pro Tyr Pro Gly Ile Pro Val
                605                     610                     615

GAA GAA CTT TTC AAG CTC CTT AAG GAA GGC CAC CGA ATG GAC AAG CCT       2223
Glu Glu Leu Phe Lys Leu Leu Lys Glu Gly His Arg Met Asp Lys Pro
                620                     625                     630

GGC AAC TGC ACC AAT GAG CTG TAT ACA ATG ATG ACG GAC TGC TGG CGT       2271
Gly Asn Cys Thr Asn Glu Leu Tyr Thr Met Met Thr Asp Cys Trp Arg
        635                     640                     645

GCT GTG CCC TCG CAA AGA CCC ACT TTC AAG CAG CTT GTT GAG GAT CTA       2319
Ala Val Pro Ser Gln Arg Pro Thr Phe Lys Gln Leu Val Glu Asp Leu
650                     655                     660                 665

GAC CGA ATC CTC ACG CAA ACG ACC AAT GAG GAG TAC CTG GAC CTC AAC       2367
Asp Arg Ile Leu Thr Gln Thr Thr Asn Glu Glu Tyr Leu Asp Leu Asn
                670                     675                     680

AAC CCT CTG GAG CAG TAC TCG CCG AGC TAT CCG GAT ACC AGG AGT TCC       2415
Asn Pro Leu Glu Gln Tyr Ser Pro Ser Tyr Pro Asp Thr Arg Ser Ser
                685                     690                     695

TGC TCT TCT GGG GAT GAC TCT GTC TTC TCC CCG GAC GCA ATG CCC TAC       2463
Cys Ser Ser Gly Asp Asp Ser Val Phe Ser Pro Asp Ala Met Pro Tyr
                700                     705                     710

GAC CCC TGT CTT CCC AAA TCC CAA CAC ACA AAC GGC ACC ATT AAA ACA       2511
Asp Pro Cys Leu Pro Lys Ser Gln His Thr Asn Gly Thr Ile Lys Thr
                715                     720                     725

TGAGGCCACA CAACCAGCAT AGACTCCCCG TTCCACCAAG AACTGTATAT ATATATATTT     2571

TTTTTTTAAG AAAAGTATAA AACAGCAGAA AACTAGCTTG GCACTTCTTA CTTCCTGCGG     2631

AGCCTCCAGC AGCCAGGGAG TGTGGGAGTC TCTGCCACGG ATCC                     2675

(2) INFORMATION FOR SEQ ID NO:6:

(i) SEQUENCE CHARACTERISTICS:
```

(A) LENGTH: 729 amino acids
(B) TYPE: amino acid
(D) TOPOLOGY: linear (ii) MOLECULE TYPE: protein (xi) SEQUENCE DESCRIPTION: SEQ ID NO:6:

```
Met Phe Ser Trp Ser Tyr Leu Met Gly Leu Val Met Val Ala Thr Ala
 1               5                  10                  15

Thr Leu Ser Leu Ala Arg Pro Ser Tyr Asn Ile Ala Glu Asp Thr Thr
             20                  25                  30

Leu Glu Pro Glu Asp Ala Asn Ser Ser Gly Asp Asp Glu Asp Asp Asn
         35                  40                  45

Asp Gly Ser Glu Asp Phe Thr Asn Asp Asn Asn His Met Arg Ala Pro
 50                  55                  60

Tyr Trp Thr Asn Thr Glu Lys Leu Glu Lys Lys Leu His Ala Val Pro
 65                  70                  75                  80

Ala Ala Asn Thr Val Lys Phe Arg Cys Pro Ala Gly Gly Asn Pro Thr
                 85                  90                  95

Pro Ser Met Arg Trp Leu Lys Asn Gly Lys Glu Phe Lys Gln Glu His
                100                 105                 110

Arg Ile Gly Gly Phe Lys Val Arg Ser Gln His Phe Ser Leu Ile Met
            115                 120                 125

Glu Ser Val Val Pro Ser Asp Glu Gly Asn Tyr Thr Cys Ile Met Glu
130                 135                 140

Asn Glu Tyr Gly Ser Ile Asn His Thr Tyr His Leu Asp Val Val Glu
145                 150                 155                 160

Arg Ser Pro His Arg Pro Ile Leu Gln Ala Gly Leu Pro Ala Asn Thr
                165                 170                 175

Thr Thr Lys Val Gly Gly Asp Ala Glu Phe Val Cys Lys Val Tyr Ser
                180                 185                 190

Asp Ala Gln Pro His Ile Gln Trp Ile Arg His Phe Glu Leu Asn Gly
            195                 200                 205

Ser Lys Ile Gly Pro Asp Gly His Pro Tyr Leu Lys Val Leu Lys Ala
210                 215                 220

Ala Gly Val Asn Thr Thr Asp Lys Glu Ile Glu Val Leu Tyr Val Arg
225                 230                 235                 240

Asn Val Ser Phe Glu Asp Ala Gly Glu Tyr Thr Cys Leu Ala Gly Asn
                245                 250                 255

Ser Thr Gly Ile Ser Tyr His Thr Ala Trp Leu Thr Val Leu Pro Asp
                260                 265                 270

Glu Glu Arg Glu Leu Asp Ser Ser Glu Tyr Thr Glu Ile Ala Ile
            275                 280                 285

Tyr Cys Val Gly Gly Phe Leu Ile Thr Cys Met Ile Gly Thr Ile Met
290                 295                 300

Val Cys His Met Lys Gly Arg Gly Lys Lys Ser Asp Phe Ser Ser Pro
305                 310                 315                 320

Pro Ala Val His Lys Leu Ser Lys Ser Leu Pro Leu Arg Arg Gln Val
                325                 330                 335

Thr Val Ser Ala Asp Ser Ser Ser Met Asn Ser Asn Thr Pro Leu
                340                 345                 350

Val Arg Ile Thr Thr Arg Leu Ser Ser Asn Asn Asp Thr His Leu Leu
            355                 360                 365

Ala Gly Val Ser Glu Tyr Glu Leu Pro Glu Asp Pro Lys Trp Glu Tyr
370                 375                 380
```

```
Pro Arg Glu Lys Leu Thr Leu Gly Lys Pro Leu Gly Glu Gly Cys Phe
385                 390                 395                 400

Gly Gln Val Val Met Ala Glu Ala Val Gly Ile Asp Lys Asp Arg Pro
            405                 410                 415

Lys Asp Ala Ala Thr Val Ala Val Lys Met Leu Lys Asp Asp Ala Thr
            420                 425                 430

Glu Lys Asp Leu Ser Asp Leu Val Ser Glu Met Glu Met Met Lys Met
        435                 440                 445

Ile Gly Lys His Lys Asn Ile Ile Asn Leu Leu Gly Ala Cys Thr Gln
450                 455                 460

Asp Gly Pro Leu Tyr Val Ile Val Glu Tyr Ala Ser Lys Gly Asn Leu
465                 470                 475                 480

Arg Glu Tyr Leu Arg Thr Arg Arg Pro Pro Gly Met Glu Tyr Ser Phe
                485                 490                 495

Asp Ile Asn Arg Ile Pro Glu Glu Gln Met Thr Phe Lys Asp Leu Val
                500                 505                 510

Ser Cys Thr Tyr Gln Leu Ala Arg Gly Met Glu Tyr Leu Ala Ser Gln
            515                 520                 525

Lys Cys Ile His Arg Asp Leu Ala Ala Arg Asn Val Leu Val Thr Glu
            530                 535                 540

Thr Asn Val Met Lys Ile Ala Asp Phe Gly Leu Ala Arg Asp Ile Asn
545                 550                 555                 560

Asn Ile Asp Tyr Tyr Lys Lys Thr Thr Asn Gly Arg Leu Pro Val Lys
                565                 570                 575

Trp Met Ala Pro Glu Ala Leu Phe Asp Arg Val Tyr Thr His Gln Ser
                580                 585                 590

Asp Val Trp Ser Phe Gly Val Leu Met Trp Glu Ile Phe Thr Leu Gly
            595                 600                 605

Gly Ser Pro Tyr Pro Gly Ile Pro Val Glu Glu Leu Phe Lys Leu Leu
610                 615                 620

Lys Glu Gly His Arg Met Asp Lys Pro Gly Asn Cys Thr Asn Glu Leu
625                 630                 635                 640

Tyr Thr Met Met Thr Asp Cys Trp Arg Ala Val Pro Ser Gln Arg Pro
                645                 650                 655

Thr Phe Lys Gln Leu Val Glu Asp Leu Asp Arg Ile Leu Thr Gln Thr
            660                 665                 670

Thr Asn Glu Glu Tyr Leu Asp Leu Asn Asn Pro Leu Glu Gln Tyr Ser
        675                 680                 685

Pro Ser Tyr Pro Asp Thr Arg Ser Ser Cys Ser Ser Gly Asp Asp Ser
690                 695                 700

Val Phe Ser Pro Asp Ala Met Pro Tyr Asp Pro Cys Leu Pro Lys Ser
705                 710                 715                 720

Gln His Thr Asn Gly Thr Ile Lys Thr
                725
```

(2) INFORMATION FOR SEQ ID NO:7:

(i) SEQUENCE CHARACTERISTICS:
        (A) LENGTH: 1839 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Notophthalmus viridescens
    (D) DEVELOPMENTAL STAGE: Adult
    (F) TISSUE TYPE: Regenerating forelimb blastema
    (G) CELL TYPE: Mesenchyme and Epithelium (vii) IMMEDIATE SOURCE:
    (A) LIBRARY: lambda gt11
    (B) CLONE: MJ3-1

(viii) POSITION IN GENOME:
    (C) UNITS: bp (ix) FEATURE:
    (A) NAME/KEY: CDS
    (B) LOCATION: 1..1134

(ix) FEATURE:
    (A) NAME/KEY: 3'UTR
    (B) LOCATION: 1135..1839

(x) PUBLICATION INFORMATION:
    (A) AUTHORS: Poulin, Matthew L
    (K) RELEVANT RESIDUES IN SEQ ID NO:7: FROM 1 TO 1839

(xi) SEQUENCE DESCRIPTION: SEQ ID NO:7:

```
AAC ACC CCT CTG GTC CGG ATC ACC CGC CTT TCA TCC AGC GAT GGG CCG       48
Asn Thr Pro Leu Val Arg Ile Thr Arg Leu Ser Ser Ser Asp Gly Pro
 1               5                  10                  15

ATG TTG GCC AAT GTG TCC GAG CTG GAG CTA CCC GCT GAT CCG AAA TGG       96
Met Leu Ala Asn Val Ser Glu Leu Glu Leu Pro Ala Asp Pro Lys Trp
             20                  25                  30

GAA TTG TCT CGT TCA CGC TTG ACT TTG GGC AAA CCT CTT GGG GAA GGA      144
Glu Leu Ser Arg Ser Arg Leu Thr Leu Gly Lys Pro Leu Gly Glu Gly
         35                  40                  45

TGC TTT GGC CAG GTG GTG ATG GTG GAT GCG GTT GGC ATT GAG AAG GAG      192
Cys Phe Gly Gln Val Val Met Val Asp Ala Val Gly Ile Glu Lys Glu
     50                  55                  60

AAG CCA AAT AAG GCC ACC ACA GTC GCT GTT AAG ATG TTG AAA GAT GAT      240
Lys Pro Asn Lys Ala Thr Thr Val Ala Val Lys Met Leu Lys Asp Asp
 65                  70                  75                  80

GCC ACC GAT AAA GAC CTG TCG GAC TTG GTC TCT GAG ATG GAA ATG ATG      288
Ala Thr Asp Lys Asp Leu Ser Asp Leu Val Ser Glu Met Glu Met Met
                 85                  90                  95

AAG ATG ATT GGG AAG CAC AAA AAC ATC ATT AAT CTC CTG GGA GCC TGC      336
Lys Met Ile Gly Lys His Lys Asn Ile Ile Asn Leu Leu Gly Ala Cys
            100                 105                 110

ACA CAG GAT GGC CCA CTC TAT GTG TTG GTG GAA TAT GCA TCC AAA GGA      384
Thr Gln Asp Gly Pro Leu Tyr Val Leu Val Glu Tyr Ala Ser Lys Gly
        115                 120                 125

AAC TTG CGG GAG TAC CTG AGG GCC CGA CGC CCT CCT GGC ATG GAT TAC      432
Asn Leu Arg Glu Tyr Leu Arg Ala Arg Arg Pro Pro Gly Met Asp Tyr
    130                 135                 140

TCC TTT GAC ACC TGC AAA CTT CCC GAA GAG CAG TTG ACC TTC AAG GAC      480
Ser Phe Asp Thr Cys Lys Leu Pro Glu Glu Gln Leu Thr Phe Lys Asp
145                 150                 155                 160

CTG GTG TCC TGT GCC TAT CAG GTG GCC CGC GGC ATG GAG TAC CTG GCC      528
Leu Val Ser Cys Ala Tyr Gln Val Ala Arg Gly Met Glu Tyr Leu Ala
                165                 170                 175

TCT CAG AAG TGC ATA CAC CGA GAT CTG GCA GCC CGG AAC GTG CTA GTG      576
Ser Gln Lys Cys Ile His Arg Asp Leu Ala Ala Arg Asn Val Leu Val
            180                 185                 190

ACG GAT GAC AAC GTT ATG AAG ATT GCT GAT TTT GGC CTG GCA AGA GAT      624
Thr Asp Asp Asn Val Met Lys Ile Ala Asp Phe Gly Leu Ala Arg Asp
        195                 200                 205
```

```
GTG CAC AAC ATC GAC TAC TAC AAG AAA ACC ACA AAT GGT CGA CTG CCT      672
Val His Asn Ile Asp Tyr Tyr Lys Lys Thr Thr Asn Gly Arg Leu Pro
    210                 215                 220

GTG AAG TGG ATG GCT CCA GAG GCT TTG TTC GAC CGG GTC TAC ACT CAC      720
Val Lys Trp Met Ala Pro Glu Ala Leu Phe Asp Arg Val Tyr Thr His
225                 230                 235                 240

CAA AGC GAT GTA TGG TCG TTT GGA GTG CTT CTG TGG GAG ATC TTC ACG      768
Gln Ser Asp Val Trp Ser Phe Gly Val Leu Leu Trp Glu Ile Phe Thr
                245                 250                 255

CTG GGA GGC TCA CCG TAC CCT GGA ATC CCG GTG GAA GAA CTC TTT AAG      816
Leu Gly Gly Ser Pro Tyr Pro Gly Ile Pro Val Glu Glu Leu Phe Lys
            260                 265                 270

CTG TTA AAA GAA GGG CAT CGA ATG GAC AAG CCA GCA AAC TGC ACG CAT      864
Leu Leu Lys Glu Gly His Arg Met Asp Lys Pro Ala Asn Cys Thr His
        275                 280                 285

GAG CTG TAT ATG ATC ATG CGA GAG TGT TGG CAT GCA GTG CCA TCC CAG      912
Glu Leu Tyr Met Ile Met Arg Glu Cys Trp His Ala Val Pro Ser Gln
    290                 295                 300

CGG CCA ACC TTT AAA CAG CTA GTA GAA GAC TTG GAC CGG GTC CTT ACG      960
Arg Pro Thr Phe Lys Gln Leu Val Glu Asp Leu Asp Arg Val Leu Thr
305                 310                 315                 320

GTG ACA TCC ACT GAT GAG TAC CTC GAC CTC TCT GTG CCC TTT GAG CAG     1008
Val Thr Ser Thr Asp Glu Tyr Leu Asp Leu Ser Val Pro Phe Glu Gln
                325                 330                 335

TAT TCG CCA GCA TGC CCA GAC AGC CAC AGC AGC TGC TCT TCT GGG GAC     1056
Tyr Ser Pro Ala Cys Pro Asp Ser His Ser Ser Cys Ser Ser Gly Asp
            340                 345                 350

GAT TCG GTC TTT ACA CAC GAC CTG CCC GAG GAG CCC TGC CTT CCC AAG     1104
Asp Ser Val Phe Thr His Asp Leu Pro Glu Glu Pro Cys Leu Pro Lys
        355                 360                 365

CAC CAG CAA CAC ATT GGA GGT ACC AGA ACA TGAGTGCTGA AGGACAAAGA      1154
His Gln Gln His Ile Gly Gly Thr Arg Thr
    370                 375

TCCAAACCAA CCCAAGCATG TAGGCTTCGA GGCGCATGGA CAGACCATCC GGAAGGGCGG    1214

TTTCGCTGGA CGGAGCCCAT GAGTGAAAGA AACCTTTTTT TCTTTCTTTG AGACGTAGGT    1274

TTTTTTACAT GCTGTACAAG AAGTCATGAA GCACTGTTTG GCCTGAAGGA CCTAATCTCT    1334

TGCCAAGATA TAAATATATA TGTGTGTCTG TGTGTGTATA TATATATATA TTTTGAAAGC    1394

AGAATGTTTA ATCTAGAGGT ATGGACTTCT TGACCTCTAG TAATGTAATA CAGTGTGCCA    1454

GAGTTGCCAA TCTGTGCCTA AGAATGCCAA GAGGAGCAAA GTTTAAAGAA GAAAAAAACT    1514

ATAAAGGAAA AAAGAAACTA TAGTGAAGAA TGTAAACCTG TTAACTTTAT GCAATCTGTG    1574

CATTAACCTT TTTGGAGAAG CCAAAAGGAA CGTGGCCTAC AAATGTTATG CTTTTTCCAG    1634

TTGAGGTAGT TTGGTACATT TCATTTTTT TGTTGCCTTG AACTGTTGTA AGTTTTTTTC    1694

TATGGAAAAC TTGGCCTTAA AATTTCGAAA CCCCCCCTAT AATTTTGTCT TTGAGAGAG    1754

AAAGATTGCA GTGGATTAAT AGGCATGTTA AAGTTGACAT TTTCAAAGGT GATTGAGGTA    1814

ATAGACAAAT GAGGAACCGG AATTC                                         1839

(2) INFORMATION FOR SEQ ID NO:8:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO:8:
```

```
Asn Thr Pro Leu Val Arg Ile Thr Arg Leu Ser Ser Asp Gly Pro
 1               5                  10                 15

Met Leu Ala Asn Val Ser Glu Leu Glu Leu Pro Ala Asp Pro Lys Trp
             20                  25                  30

Glu Leu Ser Arg Ser Arg Leu Thr Leu Gly Lys Pro Leu Gly Glu Gly
             35                  40                  45

Cys Phe Gly Gln Val Val Met Val Asp Ala Val Gly Ile Glu Lys Glu
 50                  55                  60

Lys Pro Asn Lys Ala Thr Thr Val Ala Val Lys Met Leu Lys Asp Asp
 65                  70                  75                  80

Ala Thr Asp Lys Asp Leu Ser Asp Leu Val Ser Glu Met Glu Met Met
                 85                  90                  95

Lys Met Ile Gly Lys His Lys Asn Ile Ile Asn Leu Leu Gly Ala Cys
            100                 105                 110

Thr Gln Asp Gly Pro Leu Tyr Val Leu Val Glu Tyr Ala Ser Lys Gly
        115                 120                 125

Asn Leu Arg Glu Tyr Leu Arg Ala Arg Arg Pro Pro Gly Met Asp Tyr
        130                 135                 140

Ser Phe Asp Thr Cys Lys Leu Pro Glu Glu Gln Leu Thr Phe Lys Asp
145                 150                 155                 160

Leu Val Ser Cys Ala Tyr Gln Val Ala Arg Gly Met Glu Tyr Leu Ala
                165                 170                 175

Ser Gln Lys Cys Ile His Arg Asp Leu Ala Ala Arg Asn Val Leu Val
            180                 185                 190

Thr Asp Asp Asn Val Met Lys Ile Ala Asp Phe Gly Leu Ala Arg Asp
        195                 200                 205

Val His Asn Ile Asp Tyr Tyr Lys Lys Thr Thr Asn Gly Arg Leu Pro
        210                 215                 220

Val Lys Trp Met Ala Pro Glu Ala Leu Phe Asp Arg Val Tyr Thr His
225                 230                 235                 240

Gln Ser Asp Val Trp Ser Phe Gly Val Leu Leu Trp Glu Ile Phe Thr
                245                 250                 255

Leu Gly Gly Ser Pro Tyr Pro Gly Ile Pro Val Glu Glu Leu Phe Lys
            260                 265                 270

Leu Leu Lys Glu Gly His Arg Met Asp Lys Pro Ala Asn Cys Thr His
        275                 280                 285

Glu Leu Tyr Met Ile Met Arg Glu Cys Trp His Ala Val Pro Ser Gln
        290                 295                 300

Arg Pro Thr Phe Lys Gln Leu Val Glu Asp Leu Asp Arg Val Leu Thr
305                 310                 315                 320

Val Thr Ser Thr Asp Glu Tyr Leu Asp Leu Ser Val Pro Phe Glu Gln
                325                 330                 335

Tyr Ser Pro Ala Cys Pro Asp Ser His Ser Ser Cys Ser Ser Gly Asp
            340                 345                 350

Asp Ser Val Phe Thr His Asp Leu Pro Glu Glu Pro Cys Leu Pro Lys
        355                 360                 365

His Gln Gln His Ile Gly Gly Thr Arg Thr
370                 375
```

(2) INFORMATION FOR SEQ ID NO:9:

(i) SEQUENCE CHARACTERISTICS:
        (A) LENGTH: 2681 base pairs
        (B) TYPE: nucleic acid
        (C) STRANDEDNESS: double
        (D) TOPOLOGY: linear

```
       (ii) MOLECULE TYPE: cDNA (iii) HYPOTHETICAL: NO (iv) ANTI-SENSE: NO (vi) ORIGINAL SOURCE:
            (A) ORGANISM: Notophthalmus viridescens
            (D) DEVELOPMENTAL STAGE: Adult
            (F) TISSUE TYPE: Regenerating forelimb blastema
            (G) CELL TYPE: Mesenchyme and Epithelium (vii) IMMEDIATE SOURCE:
            (A) LIBRARY: lambda gt11
            (B) CLONE: KP19-1

(viii) POSITION IN GENOME:
            (C) UNITS: bp (ix) FEATURE:
            (A) NAME/KEY: 5'UTR
            (B) LOCATION: 1..324

(ix) FEATURE:
            (A) NAME/KEY: CDS
            (B) LOCATION: 325..2517

(ix) FEATURE:
            (A) NAME/KEY: 3'UTR
            (B) LOCATION: 2518..2681

(x) PUBLICATION INFORMATION:
            (A) AUTHORS: Poulin, Matthew L
                    Chiu, Ing-Ming
            (B) TITLE: Nucleotide sequences of two newt
                (Notophthalmus viridescens) fibroblast growth
                    factor receptor-2 variants
            (C) JOURNAL: Biochim. Biophys. Acta
            (D) VOLUME: 1220
            (F) PAGES: 209-211
            (G) DATE: 1994
            (K) RELEVANT RESIDUES IN SEQ ID NO:9: FROM 1 TO 2681

(xi) SEQUENCE DESCRIPTION: SEQ ID NO:9:

GAATTCCCGA CTGTTTCCCA CGGAATAGGC TCTTGGATTA GCAGTATTTT CCCTTCCTAC      60

CAGTTTTGGG GGGTGTCGGT CGCACCCCCC ACCTAGCTCT GGATAGAAGC ACGTCCTGTA     120

CCTCGGCCGC CCCAGAGCTG GGGGCCTGCG CCGGTCTTCG CCCCCCTGGC TTCTCTCCAC     180

GCCAGAGGTG GTGCACGCTT CAGAAGGTCT CTGATTTGTG GCGGTGAAGA CCCTGGTTGC     240

AGCTCATGCT GGCGCAGAGG CCTTCTGATG GAAGAAAGT  CCACATGGCG ATGCAGGGCA     300

GGACCGGGGC GTGGCATTGA GAGG ATG TTC AGC TGG AGT TAT CTT ATG GGC       351
                          Met Phe Ser Trp Ser Tyr Leu Met Gly
                            1               5

CTG GTC ATG GTT GCC ACG GCA ACA CTT TCT CTA GCA AGG CCA TCG TAC      399
Leu Val Met Val Ala Thr Ala Thr Leu Ser Leu Ala Arg Pro Ser Tyr
 10              15                  20                  25

AAC ATT GCA GAA GAT ACT ACA CTG GAA CCA GAA GAT GCA AAC TCA TCA      447
Asn Ile Ala Glu Asp Thr Thr Leu Glu Pro Glu Asp Ala Asn Ser Ser
                 30                  35                  40

GGG GAT GAT GAA GAC GAC AAC GAC GGC TCG GAA GAT TTC ACA AAT GAC      495
Gly Asp Asp Glu Asp Asp Asn Asp Gly Ser Glu Asp Phe Thr Asn Asp
             45                  50                  55

AAC AAC CAC ATG AGG GCT CCG TAC TGG ACG AAT ACA GAA AAA TTG GAA      543
Asn Asn His Met Arg Ala Pro Tyr Trp Thr Asn Thr Glu Lys Leu Glu
         60                  65                  70

AAG AAA CTC CAT GCT GTG CCC GCT GCC AAC ACT GTG AAG TTC CGC TGT      591
Lys Lys Leu His Ala Val Pro Ala Ala Asn Thr Val Lys Phe Arg Cys
     75                  80                  85
```

```
CCA GCC GGT GGC AAC CCT ACG CCC TCC ATG AGG TGG CTG AAG AAC GGC      639
Pro Ala Gly Gly Asn Pro Thr Pro Ser Met Arg Trp Leu Lys Asn Gly
 90              95                 100                 105

AAG GAG TTC AAG CAG GAG CAC CGC ATT GGC GGC TTC AAG GTA CGT AGT      687
Lys Glu Phe Lys Gln Glu His Arg Ile Gly Gly Phe Lys Val Arg Ser
                110                 115                 120

CAA CAC TTC AGC CTG ATC ATG GAG AGC GTG GTT CCC TCT GAC GAG GGC      735
Gln His Phe Ser Leu Ile Met Glu Ser Val Val Pro Ser Asp Glu Gly
            125                 130                 135

AAC TAC ACC TGT ATC ATG GAG AAC GAG TAT GGA TCC ATC AAT CAC ACC      783
Asn Tyr Thr Cys Ile Met Glu Asn Glu Tyr Gly Ser Ile Asn His Thr
        140                 145                 150

TAC CAC CTG GAT GTT GTC GAG CGG TCA CCC CAC CGG CCA ATA CTC CAA      831
Tyr His Leu Asp Val Val Glu Arg Ser Pro His Arg Pro Ile Leu Gln
    155                 160                 165

GCT GGG CTT CCG GCA AAC ACA ACC ACA AAA GTT GGG GGC GAT GCA GAG      879
Ala Gly Leu Pro Ala Asn Thr Thr Thr Lys Val Gly Gly Asp Ala Glu
170                 175                 180                 185

TTT GTT TGC AAA GTC TAC AGT GAC GCA CAG CCA CAT ATC CAA TGG ATT      927
Phe Val Cys Lys Val Tyr Ser Asp Ala Gln Pro His Ile Gln Trp Ile
                190                 195                 200

CGA CAT TTT GAG CTG AAT GGC AGT AAA ATT GGA CCT GAC GGG CAT CCC      975
Arg His Phe Glu Leu Asn Gly Ser Lys Ile Gly Pro Asp Gly His Pro
            205                 210                 215

TAT CTG AAA GTG CTA AAG CGC TCT GGA ATT AAT AGC TCC AAT GCC GAA     1023
Tyr Leu Lys Val Leu Lys Arg Ser Gly Ile Asn Ser Ser Asn Ala Glu
        220                 225                 230

GTT CTG ACC CTG CAT AAC GTG ACT GAG GCG GAC CGG GGC CAG TAC ACA     1071
Val Leu Thr Leu His Asn Val Thr Glu Ala Asp Arg Gly Gln Tyr Thr
    235                 240                 245

TGC AAA GTC TCC AAT TAT ATT GGG GAG GCC AAC CAG TCT GCC TGG CTC     1119
Cys Lys Val Ser Asn Tyr Ile Gly Glu Ala Asn Gln Ser Ala Trp Leu
250                 255                 260                 265

ACG GTG CTG CCT GCA TCA GAG AAA GAT GAA GAA CGG GAA CTG GAT TCA     1167
Thr Val Leu Pro Ala Ser Glu Lys Asp Glu Glu Arg Glu Leu Asp Ser
                270                 275                 280

TCA TCG GAG TAT ACG GAA ATC GCC ATC TAC TGT GTG GGA GGC TTC CTG     1215
Ser Ser Glu Tyr Thr Glu Ile Ala Ile Tyr Cys Val Gly Gly Phe Leu
            285                 290                 295

ATC ACC TGC ATG ATT GGC ACA ATC ATG GTG TGC CAC ATG AAG GGC AGA     1263
Ile Thr Cys Met Ile Gly Thr Ile Met Val Cys His Met Lys Gly Arg
        300                 305                 310

GGC AAG AAG TCT GAC TTC AGC AGC CCA CCC GCT GTG CAC AAG CTG AGC     1311
Gly Lys Lys Ser Asp Phe Ser Ser Pro Pro Ala Val His Lys Leu Ser
    315                 320                 325

AAG AGT CTC CCC CTG CGC AGA CAG GTA ACA GTG TCT GCT GAC TCC AGC     1359
Lys Ser Leu Pro Leu Arg Arg Gln Val Thr Val Ser Ala Asp Ser Ser
330                 335                 340                 345

TCT TCT ATG AAC TCC AAC ACT CCA CTG GTC CGG ATC ACC ACT CGC CTG     1407
Ser Ser Met Asn Ser Asn Thr Pro Leu Val Arg Ile Thr Thr Arg Leu
                350                 355                 360

TCT TCC AAC AAT GAC ACC CAC TTG CTG GCC GGG GTC TCC GAG TAT GAG     1455
Ser Ser Asn Asn Asp Thr His Leu Leu Ala Gly Val Ser Glu Tyr Glu
            365                 370                 375

CTG CCA GAG GAC CCC AAG TGG GAG TAT CCA AGG GAA AAG CTC ACG CTG     1503
Leu Pro Glu Asp Pro Lys Trp Glu Tyr Pro Arg Glu Lys Leu Thr Leu
        380                 385                 390

GGG AAG CCC CTG GGC GAA GGC TGC TTC GGG CAG GTG GTG ATG GCA GAG     1551
Gly Lys Pro Leu Gly Glu Gly Cys Phe Gly Gln Val Val Met Ala Glu
    395                 400                 405
```

-continued

| | |
|---|---|
| GCG GTG GGC ATC GAC AAG GAC CGG CCC AAA GAT GCA GCG ACC GTG GCA<br>Ala Val Gly Ile Asp Lys Asp Arg Pro Lys Asp Ala Ala Thr Val Ala<br>410                            415                    420                       425 | 1599 |
| GTG AAG ATG CTG AAA GAC GAT GCA ACC GAG AAG GAT CTT TCT GAT CTG<br>Val Lys Met Leu Lys Asp Asp Ala Thr Glu Lys Asp Leu Ser Asp Leu<br>                     430                        435                       440 | 1647 |
| GTG TCT GAG ATG GAA ATG ATG AAG ATG ATT GGG AAG CAT AAA AAT ATC<br>Val Ser Glu Met Glu Met Met Lys Met Ile Gly Lys His Lys Asn Ile<br>                445                        450                      455 | 1695 |
| ATC AAT CTT CTA GGA GCG TGC ACC CAA GAT GGC CCA CTC TAC GTG ATA<br>Ile Asn Leu Leu Gly Ala Cys Thr Gln Asp Gly Pro Leu Tyr Val Ile<br>460                            465                          470 | 1743 |
| GTC GAA TAT GCC TCC AAG GGG AAC TTG CGT GAA TAC TTG CGC ACC CGC<br>Val Glu Tyr Ala Ser Lys Gly Asn Leu Arg Glu Tyr Leu Arg Thr Arg<br>     475                        480                      485 | 1791 |
| CGC CCA CCT GGC ATG GAG TAC TCC TTT GAC ATC AAC AGA ATT CCT GAA<br>Arg Pro Pro Gly Met Glu Tyr Ser Phe Asp Ile Asn Arg Ile Pro Glu<br>490                            495                    500                    505 | 1839 |
| GAG CAG ATG ACC TTC AAG GAC CTA GTG TCT TGC ACG TAC CAA CTG GCC<br>Glu Gln Met Thr Phe Lys Asp Leu Val Ser Cys Thr Tyr Gln Leu Ala<br>                     510                        515                    520 | 1887 |
| AGG GGA ATG GAG TAC CTG GCA TCA CAG AAG TGC ATC CAT CGG GAC TTG<br>Arg Gly Met Glu Tyr Leu Ala Ser Gln Lys Cys Ile His Arg Asp Leu<br>                525                        530                    535 | 1935 |
| GCA GCT CGG AAT GTC TTG GTG ACG GAA ACC AAC GTC ATG AAA ATT GCA<br>Ala Ala Arg Asn Val Leu Val Thr Glu Thr Asn Val Met Lys Ile Ala<br>540                            545                    550 | 1983 |
| GAT TTT GGT TTG GCC CGA GAC ATC AAC AAC ATC GAC TAC TAC AAA AAA<br>Asp Phe Gly Leu Ala Arg Asp Ile Asn Asn Ile Asp Tyr Tyr Lys Lys<br>     555                        560                    565 | 2031 |
| ACA ACC AAT GGC CGG CTC CCC GTG AAG TGG ATG GCT CCC GAG GCG CTG<br>Thr Thr Asn Gly Arg Leu Pro Val Lys Trp Met Ala Pro Glu Ala Leu<br>570                            575                    580                    585 | 2079 |
| TTT GAC AGA GTC TAC ACA CAT CAG AGT GAC GTC TGG TCT TTC GGT GTG<br>Phe Asp Arg Val Tyr Thr His Gln Ser Asp Val Trp Ser Phe Gly Val<br>                     590                        595                    600 | 2127 |
| CTT ATG TGG GAG ATC TTC ACA CTG GGG GGT TCC CCA TAC CCT GGA ATT<br>Leu Met Trp Glu Ile Phe Thr Leu Gly Gly Ser Pro Tyr Pro Gly Ile<br>                605                        610                    615 | 2175 |
| CCA GTT GAA GAA CTT TTC AAG CTC CTT AAG GAA GGC CAC CGA ATG GAC<br>Pro Val Glu Glu Leu Phe Lys Leu Leu Lys Glu Gly His Arg Met Asp<br>620                            625                    630 | 2223 |
| AAG CCT GGC AAC TGC ACC AAT GAG CTG TAT ACA ATG ATG ACG GAC TGC<br>Lys Pro Gly Asn Cys Thr Asn Glu Leu Tyr Thr Met Met Thr Asp Cys<br>     635                        640                    645 | 2271 |
| TGG CGT GCT GTG CCC TCG CAA AGA CCC ACT TTC AAG CAG CTT GTT GAG<br>Trp Arg Ala Val Pro Ser Gln Arg Pro Thr Phe Lys Gln Leu Val Glu<br>650                            655                    660                    665 | 2319 |
| GAT CTA GAC CGA ATC CTC ACG CAA ACG ACC AAT GAG GAG TAC CTG GAC<br>Asp Leu Asp Arg Ile Leu Thr Gln Thr Thr Asn Glu Glu Tyr Leu Asp<br>                     670                        675                    680 | 2367 |
| CTC AAC AAC CCT CTG GAG CAG TAC TCG CCG AGC TAT CCG GAT ACC AGG<br>Leu Asn Asn Pro Leu Glu Gln Tyr Ser Pro Ser Tyr Pro Asp Thr Arg<br>                685                        690                    695 | 2415 |
| AGT TCC TGC TCT TCT GGG GAT GAC TCT GTC TTC TCC CCG GAC GCA ATG<br>Ser Ser Cys Ser Ser Gly Asp Asp Ser Val Phe Ser Pro Asp Ala Met<br>                     700                        705                    710 | 2463 |
| CCC TAC GAC CCC TGT CTT CCC AAA TCC CAA CAC ACA AAC GGC ACC ATT<br>Pro Tyr Asp Pro Cys Leu Pro Lys Ser Gln His Thr Asn Gly Thr Ile<br>715                            720                    725 | 2511 |

```
AAA ACA TGAGGCCACA CAACCAGCAT AGACTCCCCG TTCCACCAAG AACTGTATAT    2567
Lys Thr
730

ATATATATTT TTTTTTTAAG AAAAGTATAA AACAGCAGAA AACTAGCTTG GCACTTCTTA    2627

CTTCCTGCGG AGCCTCCAGC AGCCAGGGAG TGTGGGAGTC TCTGCCACGG ATCC         2681

(2) INFORMATION FOR SEQ ID NO:10:

(i) SEQUENCE CHARACTERISTICS:
        (A) LENGTH: 731 amino acids
        (B) TYPE: amino acid
        (D) TOPOLOGY: linear (ii) MOLECULE TYPE: protein (xi) SEQUENCE DESCRIPTION: SEQ ID NO:10:

Met Phe Ser Trp Ser Tyr Leu Met Gly Leu Val Met Ala Thr Ala
 1               5                  10                  15

Thr Leu Ser Leu Ala Arg Pro Ser Tyr Asn Ile Ala Glu Asp Thr Thr
                20                  25                  30

Leu Glu Pro Glu Asp Ala Asn Ser Ser Gly Asp Asp Glu Asp Asp Asn
            35                  40                  45

Asp Gly Ser Glu Asp Phe Thr Asn Asp Asn Asn His Met Arg Ala Pro
        50                  55                  60

Tyr Trp Thr Asn Thr Glu Lys Leu Glu Lys Lys Leu His Ala Val Pro
 65                  70                  75                  80

Ala Ala Asn Thr Val Lys Phe Arg Cys Pro Ala Gly Gly Asn Pro Thr
                85                  90                  95

Pro Ser Met Arg Trp Leu Lys Asn Gly Lys Glu Phe Lys Gln Glu His
            100                 105                 110

Arg Ile Gly Gly Phe Lys Val Arg Ser Gln His Phe Ser Leu Ile Met
        115                 120                 125

Glu Ser Val Val Pro Ser Asp Glu Gly Asn Tyr Thr Cys Ile Met Glu
    130                 135                 140

Asn Glu Tyr Gly Ser Ile Asn His Thr Tyr His Leu Asp Val Val Glu
145                 150                 155                 160

Arg Ser Pro His Arg Pro Ile Leu Gln Ala Gly Leu Pro Ala Asn Thr
                165                 170                 175

Thr Thr Lys Val Gly Gly Asp Ala Glu Phe Val Cys Lys Val Tyr Ser
            180                 185                 190

Asp Ala Gln Pro His Ile Gln Trp Ile Arg His Phe Glu Leu Asn Gly
        195                 200                 205

Ser Lys Ile Gly Pro Asp Gly His Pro Tyr Leu Lys Val Leu Lys Arg
    210                 215                 220

Ser Gly Ile Asn Ser Ser Asn Ala Glu Val Leu Thr Leu His Asn Val
225                 230                 235                 240

Thr Glu Ala Asp Arg Gly Gln Tyr Thr Cys Lys Val Ser Asn Tyr Ile
                245                 250                 255

Gly Glu Ala Asn Gln Ser Ala Trp Leu Thr Val Leu Pro Ala Ser Glu
            260                 265                 270

Lys Asp Glu Glu Arg Glu Leu Asp Ser Ser Ser Glu Tyr Thr Glu Ile
        275                 280                 285

Ala Ile Tyr Cys Val Gly Gly Phe Leu Ile Thr Cys Met Ile Gly Thr
    290                 295                 300

Ile Met Val Cys His Met Lys Gly Arg Gly Lys Lys Ser Asp Phe Ser
305                 310                 315                 320
```

-continued

```
Ser Pro Pro Ala Val His Lys Leu Ser Lys Ser Leu Pro Leu Arg Arg
                325                 330                 335

Gln Val Thr Val Ser Ala Asp Ser Ser Ser Met Asn Ser Asn Thr
            340                 345                 350

Pro Leu Val Arg Ile Thr Thr Arg Leu Ser Ser Asn Asn Asp Thr His
            355                 360                 365

Leu Leu Ala Gly Val Ser Glu Tyr Glu Leu Pro Glu Asp Pro Lys Trp
370                 375                 380

Glu Tyr Pro Arg Glu Lys Leu Thr Leu Gly Lys Pro Leu Gly Glu Gly
385                 390                 395                 400

Cys Phe Gly Gln Val Val Met Ala Glu Ala Val Gly Ile Asp Lys Asp
                405                 410                 415

Arg Pro Lys Asp Ala Ala Thr Val Ala Val Lys Met Leu Lys Asp Asp
                420                 425                 430

Ala Thr Glu Lys Asp Leu Ser Asp Leu Val Ser Glu Met Glu Met Met
            435                 440                 445

Lys Met Ile Gly Lys His Lys Asn Ile Ile Asn Leu Leu Gly Ala Cys
450                 455                 460

Thr Gln Asp Gly Pro Leu Tyr Val Ile Val Glu Tyr Ala Ser Lys Gly
465                 470                 475                 480

Asn Leu Arg Glu Tyr Leu Arg Thr Arg Arg Pro Pro Gly Met Glu Tyr
                485                 490                 495

Ser Phe Asp Ile Asn Arg Ile Pro Glu Glu Gln Met Thr Phe Lys Asp
                500                 505                 510

Leu Val Ser Cys Thr Tyr Gln Leu Ala Arg Gly Met Glu Tyr Leu Ala
            515                 520                 525

Ser Gln Lys Cys Ile His Arg Asp Leu Ala Ala Arg Asn Val Leu Val
530                 535                 540

Thr Glu Thr Asn Val Met Lys Ile Ala Asp Phe Gly Leu Ala Arg Asp
545                 550                 555                 560

Ile Asn Asn Ile Asp Tyr Tyr Lys Lys Thr Thr Asn Gly Arg Leu Pro
                565                 570                 575

Val Lys Trp Met Ala Pro Glu Ala Leu Phe Asp Arg Val Tyr Thr His
                580                 585                 590

Gln Ser Asp Val Trp Ser Phe Gly Val Leu Met Trp Glu Ile Phe Thr
            595                 600                 605

Leu Gly Gly Ser Pro Tyr Pro Gly Ile Pro Val Glu Glu Leu Phe Lys
610                 615                 620

Leu Leu Lys Glu Gly His Arg Met Asp Lys Pro Gly Asn Cys Thr Asn
625                 630                 635                 640

Glu Leu Tyr Thr Met Met Thr Asp Cys Trp Arg Ala Val Pro Ser Gln
                645                 650                 655

Arg Pro Thr Phe Lys Gln Leu Val Glu Asp Leu Asp Arg Ile Leu Thr
                660                 665                 670

Gln Thr Thr Asn Glu Glu Tyr Leu Asp Leu Asn Asn Pro Leu Glu Gln
            675                 680                 685

Tyr Ser Pro Ser Tyr Pro Asp Thr Arg Ser Ser Cys Ser Ser Gly Asp
690                 695                 700

Asp Ser Val Phe Ser Pro Asp Ala Met Pro Tyr Asp Pro Cys Leu Pro
705                 710                 715                 720

Lys Ser Gln His Thr Asn Gly Thr Ile Lys Thr
                725                 730
```

(2) INFORMATION FOR SEQ ID NO:11:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Notophthalmus viridescens (vii) IMMEDIATE SOURCE:
         (B) CLONE: Oligonucleotide HBGF 306

(viii) POSITION IN GENOME:
         (C) UNITS: bp (ix) FEATURE:
         (A) NAME/KEY: CDS
         (B) LOCATION: 1..26

(x) PUBLICATION INFORMATION:
         (A) AUTHORS: Patrie, Kevin M
               Botelho, Mary Jane
               Ray, Subir K
               Mehta, Veela B
               Chiu, Ing-Ming
         (C) JOURNAL: J. Biol. Chem.
         (K) RELEVANT RESIDUES IN SEQ ID NO:11: FROM 1 TO 26

(xi) SEQUENCE DESCRIPTION: SEQ ID NO:11:

TTYACAGCNC TGACNGARAA RTTYAA                                              26

(2) INFORMATION FOR SEQ ID NO:12:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Notophthalmus viridescens (vii) IMMEDIATE SOURCE:
         (B) CLONE: Oligonucleotide HBGF 603

(viii) POSITION IN GENOME:
         (C) UNITS: bp (ix) FEATURE:
         (A) NAME/KEY: CDS
         (B) LOCATION: complement (1..23)

(x) PUBLICATION INFORMATION:
         (A) AUTHORS: Patrie, Kevin M
               Botelho, Mary Jane
               Ray, Subir K
               Mehta, Veela B
               Chiu, Ing-Ming
         (C) JOURNAL: J. Biol. Chem.
         (K) RELEVANT RESIDUES IN SEQ ID NO:12: FROM 1 TO 23

(xi) SEQUENCE DESCRIPTION: SEQ ID NO:12:

TAGGTRTTRT ARTGRTTYTC YTC                                                 23

MURINE CELL LINES WHICH OVER PRODUCE ACIDIC FIBROBLAST GROWTH FACTOR (AFGF) AND METHOD OF USING SAME

This is a divisional application Ser. No. 08/070,165 filed on May 28, 1993, now U.S. Pat. No. 5,750,365.

TECHNICAL FIELD

The present invention relates to recombinant DNA-directed synthesis of certain proteins, the recombinant DNA sequences themselves and cell lines which express the recombinant DNA and proteins. More particularly, the present invention relates to newt fibroblast growth factor CDNA and sequence and to fibroblast growth factor receptors, FGFR1, FGFR2, FGFR2 and KGFR which have been cloned from a newt (*Notophthalamus viridescens*) limb blastema cDNA library. The FGFR1 and FGFR2 have distinct roles in limb regeneration, despite their sharing a number of the FGF ligands.

The present invention was supported in part by grants from the NIH (R01 CA45611, K04 CA01369, and P30 CA16058) who may have certain rights in the invention.

BACKGROUND OF THE INVENTION

The fibroblast growth factor (FGF) family contains eight members (Basilico et al., 1992, The FGF family of growth factors and oncogenes. *Adv. Cancer Res.* 59:115–165). This reference and all references cited herein are expressly incorporated herein by reference. The two prototypic members, acidic FGF (Jaye et al., 1986, Human endothelial cell growth factor: cloning, nucleotide sequence, and chromosomal localization. *Science* 23:541–545; Wang et al., 1989, Cloning of the gene coding for human class I heparin-binding growth factor and its expression in fetal tissue. *Mol. Cell. Biol* 9:2387–2395) and basic FGF (Abraham et al., 1986, Human basic fibroblast growth factor: nucleotide sequence and genomic organization. *EMBO J.* 5:2523–2528) have no signal peptide but the remaining six members, FGF-3 (Dickson et al., 1987, Potential oncogene product related to growth factors. *Nature* 326–833; Acland et al., 1990, Subcellular fate of int-2 oncoprotein is determined by choice of initiation codon. *Nature* 343:662–665), FGF-4 (Delli-Bovi et al., 1987, An oncogene isolated by transfection of Kaposi's sarcoma DNA encodes a growth factor that is a member of the FGF family. *Cell* 50:729–737; Taira et al., 1987, cDNA sequence of human transforming gene hst and identification of the coding sequence required for transforming activity. *Proc. Natl. Acad. Sci. USA* 84:2980–2984), FGF-5 (Zhan et al., 1988, The human FGF-5 oncogene encodes a novel protein related to fibroblast growth factors. *Mol. Cell. Biol.* 8:3487–3495), FGF-6 (deLapeyriere et al., 1990, Structure, chromosome mapping, and expression of the murine FGF-6 gene. *Oncogene* 5:823–831), keratinocyte growth factor (KGF) (Finch et al., 1989, Human KGF is FGF-related with properties of a paracrine effector of epithelial cell growth. *Science* 245:752–755) and androgen-induced growth factor (AIGF) (Tanaka et al., 1992, Cloning and characterization of an androgen-induced growth factor essential for the androgen-dependent growth of mouse mammary carcinoma cells. *Proc. Natl. Acad. Sci. USA* 89:8928–8932) all have signal peptides. Various members of the FGF family are involved in cell growth, differentiation, and survival as well as embryonic induction and angiogenesis (Basilico et al., supra). Because the release of aFGF and bFGF is thought to be through dead or dying cells, it is implied that they are also involved in tissue repair. Moreover, KGF mRNA has been shown to be induced more than 160 fold during wound healing (Werner et al., 1992, Large induction of keratinocyte growth factor expression in the dermis during wound healing. *Proc. Natl. Acad. Sci. USA* 89:6896–6900).

As with most polypeptide growth factors, the FGF signal is transduced via membrane-spanning protein tyrosine kinase (PTK) receptors (Johnson et al., 1993, Structural and functional diversity in the FGF receptor multigene family, *Adv. Cancer Res.* 60:1–41). The four members of the FGF receptor family, flg/FGFR1 (Ruta et al., 1989, Receptor for acidic fibroblast growth factor is related to the tyrosine kinase encoded by the fms-like gene (FLG). *Proc. Natl. Acad. Sci. USA* 86:8722–8726; Dionne et al., 1990, Cloning and expression of two distinct high-affinity receptors cross-reacting with acidic and basic fibroblast growth factor. *EMBO J.* 9:2685–2692; Johnson et al., 1990, Diverse forms of a receptor for acidic and basic fibroblast growth factors. *Mol. Cell. Biol.* 10:4728–4736), bek/FGFR2 (Kornbluth et al., 1988, Novel tyrosine kinase identified by phosphotyrosine antibody screening of cDNA libraries. *Mol. Cell. Biol.* 8:5541–5544; Dionne et al., 1990, supra), FGFR2 (Keegan et al., 1991, Isolation of an additional member of the fibroblast growth factor receptor family, FGFR-3. *Proc. Natl. Acad. Sci. USA* 88:1095–1099), and FGFR4 (Partanen et al., 1991, FGFR-4, a novel acidic fibroblast growth factor receptor with a distinct expression pattern. *EMBO J.* 10:1347–1354) all contain three immunoglobulin (lg)-like extracellular domains (Williams et al, 1988, The immunoglobulin superfamily-domains for cell surface recognition. *Ann. Rev. Immunol.* 6:381–405). The first Ig-like domain may or may not be present due to alternative splicing, resulting in either a two or three loop variant (Mansukhani et al., 1990, A murine fibroblast growth factor (FGF) receptor expressed in CHO cells is activated by basic FGF and Kaposi FGF. *Proc. Natl. Acad. Sci. USA* 87:4378–4382; Fujita et al., 1991, The expression of two isoforms of the human fibroblast growth factor receptor (flg) is directed by alternative splicing. *Biochem. Biophys. Res. Comm.* 174:946–951). This first loop has no effect on ligand binding and its function remains unknown (Johnson et al., 1990, supra; Mansukhani et al., 1990, supra). The genes of FGFR1 and FGFR2 contain three consecutive yet mutually exclusive exons that encode the 3' half of the last Ig-like domain (Champion-Arnaud et al., 1991, Multiple mRNAs code for proteins related to the BEK fibroblast growth factor receptor. *Oncogene* 6:979–987; Eisemann et al., 1991, Alternative splicing generates at least five different isoforms of the human basic-FGF receptor. *Oncogene* 6:1195–1202; Johnson et al., 1991, The human fibroblast growth factor receptor genes: A common structural arrangement underlies the mechanisms for generating receptor forms that differ in their third immunoglobulin domain. *Mol. Cell. biol.* 11:4627–4634; Yayon et al., 1992, A confined variable region confers ligand specificity on fibroblast growth factor receptors: Implications for the origin of the immunoglobulin fold. *EMBO J.* 11:1885–1890). Alternative splicing in this region generates secreted forms of these receptors and receptors with differences in their FGF binding specifities. Splicing of the first of the three exons (IIIa) into the mRNA results in a secreted form of the receptor containing no transmembrane or PTK domain (Johnson et al., supra., 1990, 1991). If the next exon (IIIb) is spliced into the mRNA, a membrane spanning PTK receptor with a high affinity for aFGF and KGF results. When considering FGFR2, this isoform is referred to as the KGF receptor (Miki et al., 1991, Expression cDNA cloning of the KGF receptor by creation of a transforming autocrine loop. *Science* 251:72–75; 1992, Determination of ligand-binding specificity by alternative splicing: Two distinct growth factor receptors encoded by a single gene. *Proc. Natl. Acad. Sci. USA* 89:246–250; Yayon et al., 1992, supra). Inclusion of the last of these three exons (IIIc) confers high affinity to aFGF, bFGF and FGF-4

(Dionne et al., 1990, supra; Mansukhani et al., 1992, Characterization of the murine BEK fibroblast growth factor (FGF) receptor: Activation by three members of the FGF family and requirement for heparin. *Proc. Natl. Acad. Sci. USA* 89:3305–3309) but not to KGF (Miki et al., 1992, supra). This FGFR2 isoform is referred to as a "bek-like" receptor.

Expression patterns of several FGF proteins during development are well documented (Whitman et al., 1989, Growth factors in early embryogenesis. *Annu. Rev. Cell Biol.* 5:93–117; Hebert et al., 1990, Isolation of cDNAs encoding four mouse FGF family members and characterization of their expression patterns during embryogenesis. *Dev. Biol.* 138:454–463; Niswander et al., 1992, FGF-4 expression during gastrulation, myogenesis, limb and tooth development in the mouse. *Development* 114:755–768; Tannahill et al., 1992, Development expression of the Xenopus int-2 (FGF-3) gene: Activation by mesodermal and neural induction. *Development* 115:696–702). The FGFs have also been implicated in amphibian limb regeneration but their specific role in this developmental process remains obscure. When FGF is infused into the distal stump of denervated newt limbs, cell cycling is stimulated over the depressed level normally seen after denervation (Mescher et al, 1979, Mitogenic effect of a growth factor derived from myelin on denervated regenerates of newt forelimbs. *J. Exp. Zool.* 207:497–503; Gospodarowicz et al., 1980, Fibroblast growth factor and the control of vertebrate regeneration and repair. *Ann. N. Y. Acad. Sci.* 339:151–174). By binding assays and Western blotting analysis, (Boilly et al., 1991, Acidic fibroblast growth factor is present in regenerating limb blastemas of axolotis and binds specifically to blastema tissue. *Dev. Biol.* 145:302–310), showed that aFGF and its receptor(s) are present within the newt limb blastema; nevertheless, the cellular source of this growth factor was not determined. In the mouse limb bud, FGFR2 transcripts were detected in the surface ectoderm, whereas FGFR1 transcripts were distributed diffusely in the mesenchyme (Orr-Urtreger et al., 1991, Developmental expression of two murine fibroblast growth factor receptors, fig and bek. *Development* 113:1419–1434; Peters et al., 1992, Two FGF receptor genes are differentially expressed in epithelial and mesenchymal tissues during limb formation and organogenesis in the mouse. *Development* 114:233–243).

According to the present invention cDNAs of newt aFGF was isolated and characterized.

According to the present invention, cDNAs of newt FGFR1 and FGFR2, FGFR3 and KGFR were cloned. Riboprobes made from these cDNAs were used to carry out in situ hybridization at various stages of newt limb regeneration.

Further according to the present invention there is disclosed cells transfected with a DNA sequence encoding human acidic fibroblast growth factor and capable of expressing said factor.

An object of the present invention is to provide purified and synthetic forms of newt aFGF.

An additional object of the present invention is the determination of the amino acid sequence of such aFGF.

A further object of the present invention includes providing purified forms of newt aFGF and mammalian cell lines expressing FGF receptors which would be valuable to evaluate agonist and antagonist proteins such as human FGF proteins.

DISCLOSURE OF INVENTION

The cDNA coding for the human full-length aFGF have been cloned (Bunnag et al., 1991, Transformed phenotype conferred to NIH/3T3 cells by ectopic expression of heparin-binding growth factor 1/acidic fibroblast growth factor. *In Vitro Cell. Dev. Biol.* 27A:89–96; Chiu et al., 1990, Alternative splicing generates two forms of mRNA coding for human heparin-binding growth factor 1. *Oncogene* 5:755–762). A number of others have also cloned and expressed human aFGF.

During the characterization of the cell lines expressing human full-length aFGF (Bunnag et al., 1991, supra) the inventors herein surprisingly found that two cell lines (Tr31-5-1 and Tr33-1-2 which are mouse embryo NIH/3T3 cells transfected with expression vector pZIPneoSV(x) containing human aFGF cDNA and overexpress human aFGF protein, which Tr31-5-1 and Tr33-1-2 strains have been deposited with the American Type Culture Collection, 10801 University Boulevard, Manassas, Va. 20110-2209; U.S.A. with the Accession Numbers: ATCC CRL-12521 and ATCC CRL-12522, respectively), unlike their predecessor, do not respond to the mitogenic stimulation of full-length aFGF but still respond to truncated aFGF. According to the present invention cell lines are generated that will or will not respond to stimulation by aFGF. These cell lines are useful for the identification of agonists and antagonists of aFGF and other FGF proteins. Also, according to the present invention, FGF and FGF receptor (FGFR) cDNAs were isolated from species distant from human. An amphibian species commonly known as newt or salamander (*Notophthalamus viridescens*), known to regenerate their limbs after amputation, was chosen.

The present invention thus relates to novel newt aFGF cDNA and sequence, newt FGFR1 cDNA and sequence, newt FGFR2 cDNA and sequence, newt FGFR3 cDNA and sequence, newt KGFR EDNA and sequence, CHO-K1 cell lines (such as KPTr2—2) expressing newt KGFR, and mutant cell lines that become non-responsive to aFGF stimulation. These novel sequences and cell lines will substantially enhance the availability of acidic fibroblast growth factor.

BRIEF DESCRIPTION OF THE FIGURES

FIG. I is a representation of NvFGFR2 cDNA clones. The receptor molecule is graphically represented above the cDNA clones. The major restriction sites are shown between the graphic model and the EDNA clones (Bm=BamHI; Bg=BgIII; E=EcoRI; H2=HindII; P=PstI; Xb=XbaI; Xh=XhoI). The model is drawn to linear scale in relation to the cDNA sequence. The open and closed triangles represent the initiation and termination codons, respectively. The three loop structures represent the immunoglobulin (lg)-like extracellular domains and the verticle line bisecting the molecule between the first and second Ig-like domains represents the acidic domain. The open box followed by the wavy line represents the transmembrane and juxtamembrane domains and the closed box represents the tyrosine kinase domain bisected by the kinase insert. The hatched box on the cDNA clones represents sequence that codes for the KGFR isoform (IIIb) whereas the cross-hatched box on clone 110 represents the bek-like (IIIc) isoform. The clones that are made contiguous with dashed lines represent cDNA's in which the first Ig-like domain is spliced out. Clone 301 represents the three loop form of newt FGFR2.

FIGS. 2A and 2B show the nucleotide and predicted amino acid sequences of the newt FGFR2 cDNA (NvFGFR2). The hydrophobic signal sequence and transmembrane domain are double underlined. The single underline indicates potentially translated sequence. Bracketed amino acids indicate the immunoglobulin-like domain with the conserved cysteines indicated by asterisks. The alternatively spliced portion of the last Ig-like domain is indicated by a wavy underline The amino acids of the protein tyrosine kinase domain are in parentheses and the kinase insert is highlighted. The sequence presented here is the KGFR variant of FGFR2.

FIG. 3 shows a comparison of the two amino acid sequences encoded by the second half of the last Ig-like domain. FIG. 3, part A shows alignment of the amino acid sequences encoded by the newt KGFR (clones 109, 301, 302, 310) and bek (clone 110) cDNA clones. FIG. 3, part B shows alignment of the amino acid sequences of newt and human KGFR. FIG. 3, part C shows alignment of the amino acid sequences of newt and human bek. The sequences were aligned using the DNASTAR Align program. The human sequences were obtained from Miki et al., 1991, supra and Dionne et al., 1990, supra.

FIGS. 5A and 5B show the hybridization of the anti-sense riboprobe to the basal layer of the wound epithelium (we), which is shown at higher magnification in FIG. 5C and FIG. 5D, and to the cells of the periosteum (black arrows) of the bisected bone (b), shown in FIGS. 5E and 5F under higher magnification. At this stage no signal is seen over the differentiating mesenchyme cells. A, Bar=180 µm. C and E, Bar=70 µm.

DESCRIPTION OF INVENTION

Figure 1:
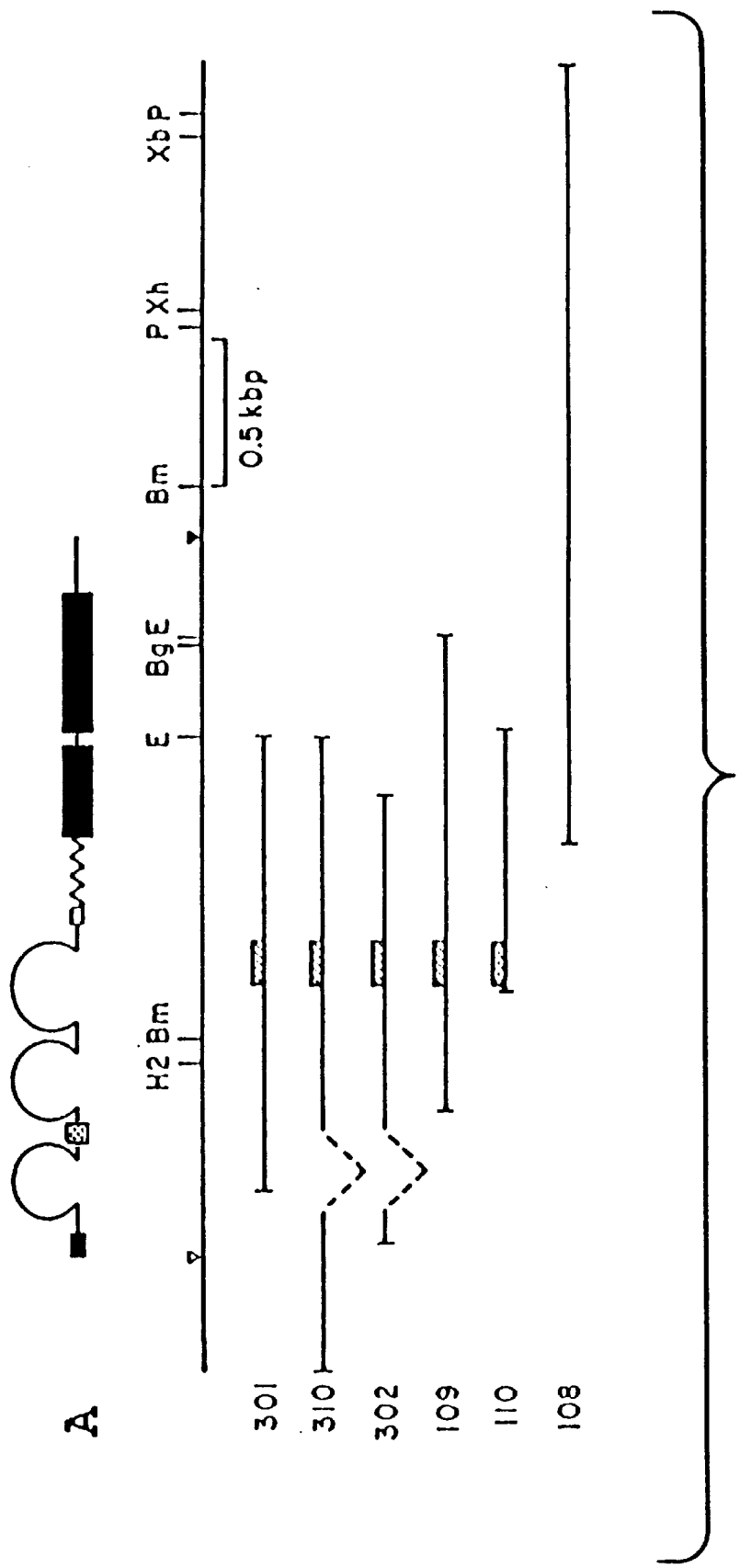

The present invention has made it possible to provide readily available quantities of newt aFGF and newt FGFR fragments. As used herein FGF means fibroblast growth factor or its fragments produced by cell or cell-free culture systems. The FGF is in a bioactive form which means it has the capacity to influence cellular growth differentiation and survival as well as embryonic induction and angiogenesis.

Different alleles of FGF exist in nature. These variations are characterized by differences in nucleotide sequences of the structure gene coding for proteins of identical biological function. According to the present invention it is possible to produce analogs having single or multiple amino acid deletions, additions, substitutions or replacements. It is to be understood that all such allelic modifications, variations and analogs resulting in derivatives of FGF which retain the biologically active properties of newt FGF are included with the scope of this invention.

Further, according to the present invention expression vectors first two vectors which are capable of transcribing and translating DNA sequences contained within the vector where such sequences are linked to other regulatory sequences (such as promoters) capable of affecting the DNA sequence's expression it is understood that these expression vectors are replicable in host organisms or systems as an integral part of the chromosomal DNA, as a bacteriophage or as an episome.

While the present invention discloses particular expression vectors which are particularly suitable for use in the invention, other expression vectors such as bacteriophages and viruses which normally inhabit and replicate in bacterial are useful. It is further understood that expression vectors such as plasmids or other forms of expression vectors which serve an equivalent function are suitable for use with the present invention.

The host cells useful with the present invention include various prokaryotic and eukaryotic organisms. Prokaryotic organisms such as E. coli are useful in the present invention. It is to be understood that other microbial strains which are compatible with the desired vectors can be utilized. It is to be understood that various control elements used for expression of foreign DNA sequences and combinations of these control elements can be used with the present invention.

Further host organisms include eukaryotic microbe yeast and cell lines derived from multi-cellular organisms. Various control elements useful in eukaryotic organisms and cell lines from multi-cellular organisms can be utilized with the present invention.

The principles for the present invention will be explained by this detailed description of the preferred embodiments together with the following examples.

A. Cloning of the Newt aFGF cDNA

The newt aFGF gene is too divergent from the human gene to be detected with heterologous probes in Southern hydridization. The newt aFGF cDNA was cloned by reverse transcription and polymerase chain reaction (RT-PCR). The degenerate synthetic oligonucleotides were designed from the most conservative region of aFGF among different species (upstream primer 306, 5'-TTY ACA GCN CTG ACN GAR AAR TTY AA-3' (SEQ ID NO:11); downstream primer 603, 5'-TAG GTR TTR TAR TGR TTY TCY TC-3' (SEQ ID NO:12); R=purine, Y=pyrimidine, N=any base) and carried out RT-PCR to isolate the aFGF EDNA from newt brain RNA. Newt brain total RNA (0.5 μg) was combined with 1.5 μM of the downstream primer and *Thermus thermophilus* (Tth) polymerase in the presence of 1 mM MnCl$_2$ and 200 μM dNTP. This was incubated for 15 min at 60° C. to allow the reverse transcription to take place. The upstream primer was then added at a concentration of 0.3 μM along with a Mn++ chelator and MgCl$_2$ at a concentration of 2 mM to allow DNA polymerization to take place. The mixture was then cycled between 1 min at 94° C. and 1 min at 50° C. for 30 cycles. One fifth of the reaction mix was analyzed by electrophoresis on a 3% agarose gel followed by Southern analysis. The filter was hybridized with the human aFGF cDNA and a band of 300 bp was observed on the X-ray film but could not be visualized on the ethidium bromide stained gel. A second fifth was electrophoresed on a 3% agarose gel and the region between 280 and 340 bp was isolated and purified with Geneclean. A PCR reaction was then performed using 0.3 μM of both primers under the same cycling conditions above. One fifth was analyzed on a 3% agarose gel and a band of 310 bp was observed, isolated and subcloned into the SmaI site of pBluescript SK(+). Three subclones were completely sequenced and the results indicate that a 311 bp cDNA fragment representing the newt aFGF EDNA was isolated and characterized, as shown in Sequence ID No. 1 and 2.

B. Cloning of the Newt FGFR1 cDNA, FGFR2 cDNA, FGFR3 cDNA and KGFR cDNA.

According to the present invention, DNA sequences encoding all or part of the polypeptide sequence of newt fibroblast growth factor (NvFGFR1 and NvFGFR2) have been isolated and characterized as follows.

A newt forelimb blastema cDNA library was screened under reduced stringency with a partial human cDNA fragment of the FGFR1 gene. Four lambda clones, 102, 108, 109 and 110, were purified and sequenced. The sequences show that three clones, 108, 109 and 110 overlap each other and are most homologous to the FGFR2 cDNAs of different species, as shown in FIG. 1 and in Table 1 below. The sequence of clone 102 indicates that this cDNA is most homologous to FGFR1 cDNAs of different species as seen in Table I,

TABLE 1

| | Nucleotide sequence similarities between different members of the FGF receptor family | | | | | | |
|---|---|---|---|---|---|---|---|
| | (445–2556)[1] HUM FGFR1 | (794–2887)[2] HUM FGFR2 | (418–2460)[3] HUM FGFR3 | (410–2464)[4] HUM FGFR4 | (410–2515)[5] Ch FGFR1 | (485–2575)[6] Ch FGFR2 | (523–2571)[7] Ch FGFR3 |
| Newt FGFR1 (1–1176) | 77 | 72 | 69 | 61 | 76 | 71 | 69 |
| Newt FGFR2 (433–2517) | 69 | 78 | 68 | 62 | 69 | 78 | 68 |

The nucleotides used in the comparison are shown in parentheses and are taken from the following references: Dionne et al., 1990, Cloning and expression of two distinct high-affinity receptors cross-reacting with acidic and basic fibroblast growth factor. EMBO J. 9:2685–2692[1]; Miki et al., 1992[2], Determination of ligand-binding specificity by alternative splicing: Two distinct growth factor receptors encoded by a single gene. Proc. Natl. Acad. Sci. USA 89:246–250; Keegan et al., 1991[3], Isolation of an additional member of the fibroblast growth factor receptor family, FGFR-3. Proc. Natl. Acad. Sci. USA 88:1095–1099; Partanen et al., 1991[4], FGFR-4, a novel acidic fibroblast growth factor receptor with a distinct expression pattern. EMBO J. 10:1347–1354; Pasquale et al., 1989[5], Identification of a developmentally regulated protein-tyrosine kinase by using anti-phosphotyrosine antibodies to screen a cDNA expression library. Proc. Natl. Acad. Sci USA 86:5449–5452; Sato et al., 1991[6], Isolation of chicken-bek and a related gene; identification of structural variation in the ligand-binding domains of the FGF-receptor family. Oncogene 6:1279–1283; Pasquale, 1990[7], A distinctive family of embryonic protein-tyrosine kinase receptors. Proc. Natl. Acad. Sci. USA 87:5812–5816. The alignments and percent similarity were determined using DNASTAR's ALIGN program.

These clones all contain the cytoplasmic tyrosine kinase domain but are truncated in the extracellular ligand binding domain. Two of the newt FGFR2 clones, 109 and 110, also contain a region in the 3' half of the distal Ig-like domain that vary between them. These variants represent the newt cognates of two different isoforms of FGFR2, one homologous to bek the other to the KGFR. To obtain full-length FGFR2 cDNA clones, the 5' portion of clone 109 (240 bp EcoRI-BamHI) was used to rescreen the blastema cDNA library and three more cDNA clones were isolated, purified and sequenced. Clones 302 and 310 represent the two Ig-like loop variant of FGFR2 while Clone 301 represents a truncated form of the three loop form of FGFR2. All three 300 series cDNA clones are of the KGFR isoform.

Figure 2B:
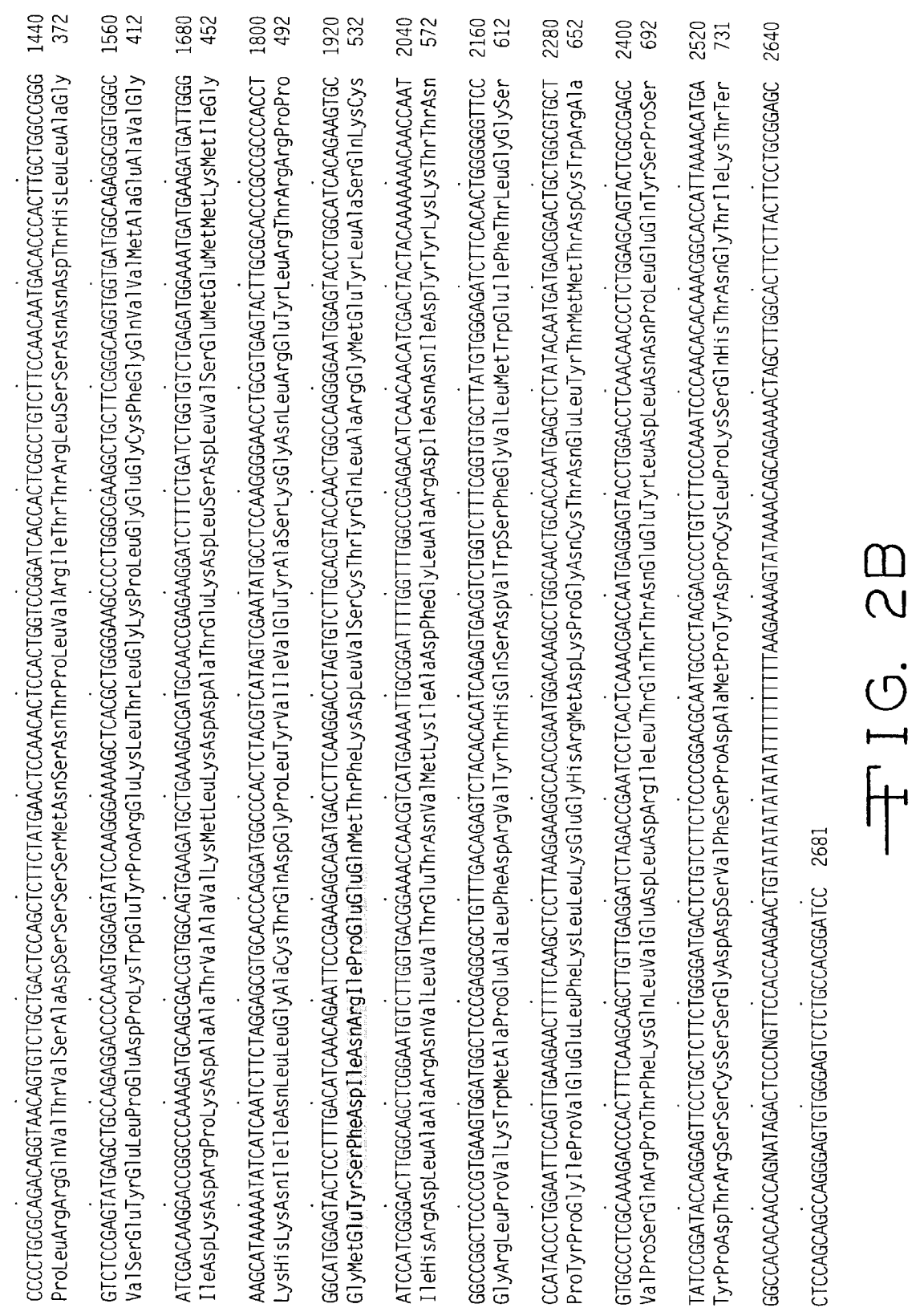

The predicted amino acid sequence for the newt two Ig-like loop variant of KGFR is shown in FIGS. 2A and 2B (Sequence ID No: 9 and 10). The sequence in the 3'-half of the last Ig-like domain represents that of the KGFR isoform, as shown in FIGS. 2A and 2B. FIG. 3, part A shows the difference between the newt KGFR-like and bek-like forms of FGFR2. The amino acid alignment, as well as the nucleotide sequence comparisons, show that the flanking regions of these cDNAs are identical whereas the region in between shares 58% amino acid similarity. It is noted that the sequence similarity is greater, 73% and 78%, respectively, as shown in FIG. 3, parts B and C, between the same isoforms of different species (newt KGFR vs. human KGFR and newt bek vs. human bek) than between the different isoforms of the same species (FIG. 3, part A). Sequence ID numbers for the DNA and predicted amino acid sequence of the bek-like newt FGFR2 are 5 and 6, respectively. The overall sequence similarity of the newt KGFR and the truncated newt FGFR1 (Sequence ID No: 3 and 4) cDNA with other human and chicken FGFR cDNAs is shown in Table 1. When the newt FGFR1 is compared with other FGF receptors, the closest similarity is with FGFR1 from other species, 77% with human and 76% with chicken FGFR1. Likewise, the newt KGFR form of FGFR2 is closest to other FGFFR2 cDNA's, 78% to both human and chicken FGFR2.

In another library screening, clone 103 (a.k.a. MJ3-1) was isolated. Sequencing analysis of MJ3-1 showed that it is most homologous to FGFR2 cDNAs of human and mouse, and therefore designated NvFGFR2 (Sequence ID Nos. 7 and 8).

Figure 4:
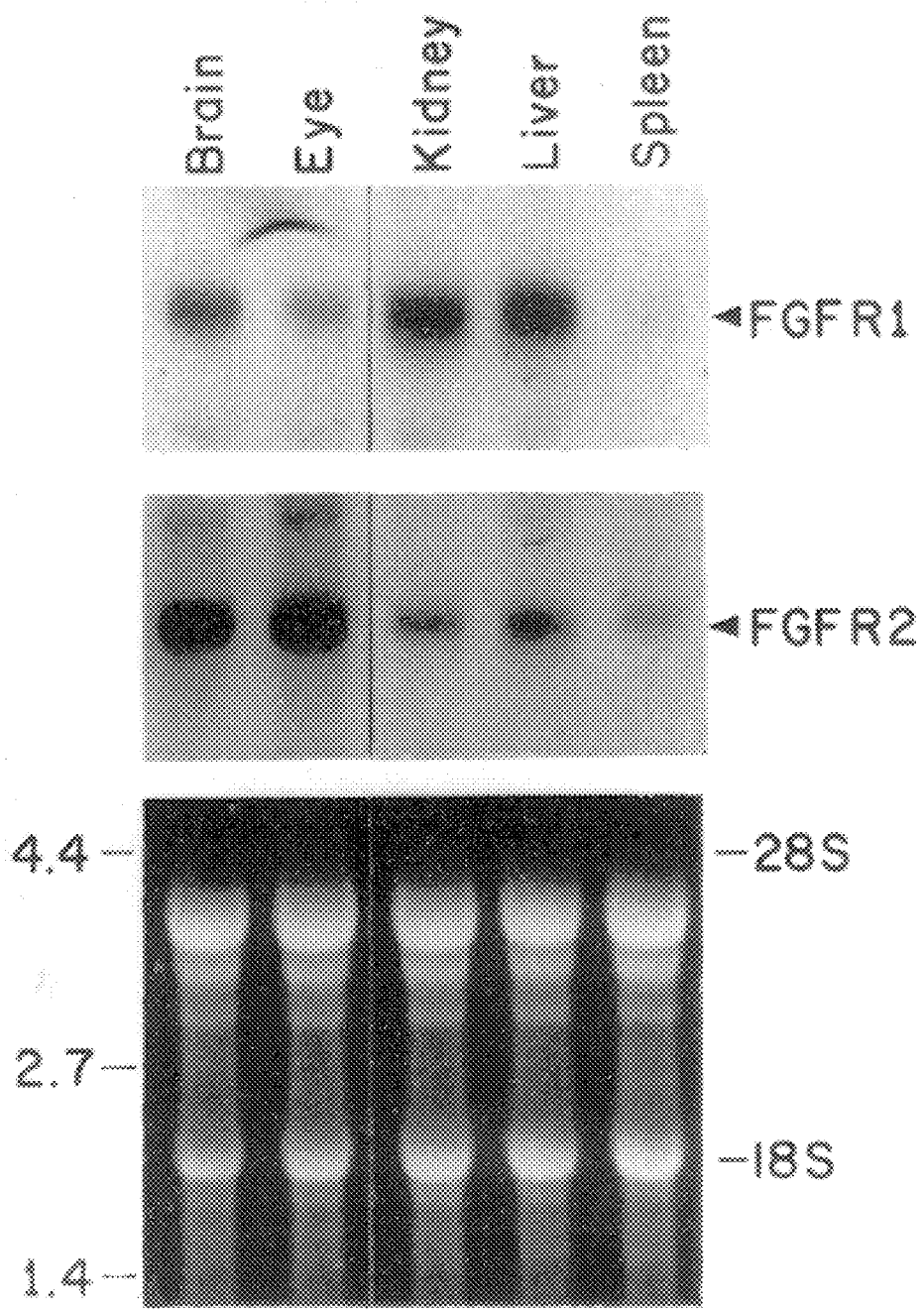
FIG. 4 shows a Northern blot analysis of newt tissues. Total RNA from newt brain, eye, kidney, liver, and spleen was hybridized to $^{32}$P-labeled antisense riboprobes used in the in situ hybridizations. A single hybridizing band was observed using either the FGFR1 or FGFR2 riboprobes. The ethidium bromide stained agarose gel is shown to indicate loading the same amount of the RNA in each lane. The neural derived brain and eye express higher levels of the 6.5 kb FGFR2 mRNA while the mesodermally derived kidney and liver express higher levels of the 4.8 kb FGFR1 mRNA. The markers on the left are in kilobases (kb) and the 28S and 18S markers on the right are where the human large and small rRNA ran on the gel. Note that the newt large rRNA runs faster than the human 28S rRNA in the gel.

Northern Hybridization—As a first step toward determining the FGFR expression pattern and specificity of the riboprobes, Northern analysis on various newt tissues was carried out. The FGFR1 and FGFR2 antisense riboprobes used for the in situ were hybridized to newt brain, eye, kidney, liver, and spleen total RNA. A single band of 4.8 kb was observed in these tissues with the FGFR1 riboprobe with the kidney and liver showing the highest intensity of signal. When the same filter was stripped and hybridized to an FGFR2 riboprobe, a single band of 6.5 kb was observed with the brain and eye showing the highest level of hybridization, as shown in FIG. 4.

In Situ Hybridization—Cryosections of regenerating newt limbs of different stages staged according to (Iten et al., 1973, Forelimb regeneration from different levels of amputation in the newt, *N. viridescen*: Length, rate, and stages. *Wilhelm Roux Arch.* 173:263–282), were hybridized to both sense and antisense $^{35}$S-labeled riboprobes, washed and exposed to photographic emulsion. The slides were developed, stained with hematoxylin and counterstained with eosin, and examined under both light- and dark- field microscopy. The fragment used to generate the FGFR2 riboprobes was a 306 bp BbsI-BamHI fragment containing the second Ig-like extracellular domains (nt. 465–770 in FIGS. 2A and 2B). This antisense riboprobe recognizes all known isoforms, generated by alternative splicing, of newt FGFR2. The newt FGFR1 specific riboprobe represents the last 73 amino acids of the carboxyl terminus and 80 nucleotides of 3'-untranslated sequence.

Figure 5A:
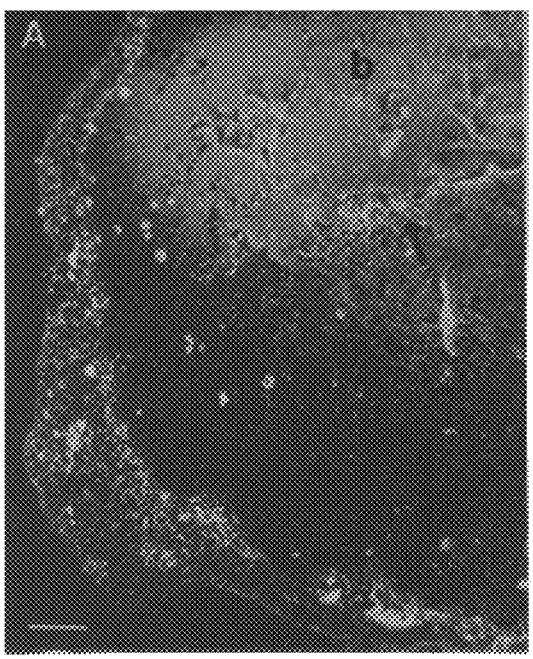
FIGS. 5A, 5B, 5C, 5D, 5E and 5F are micrographs illustrating the localization of FGFR2 mRNA in a pre-blastema regenerate. Antisense (A, C, and E) and sense (B, D, and F)$^{35}$S-labeled riboprobes were hybridized to cryo-sections of a day 10 pre-blastema stage regenerate and visualized by dark-field microscopy.
Figure 5B:
Figure 5C:
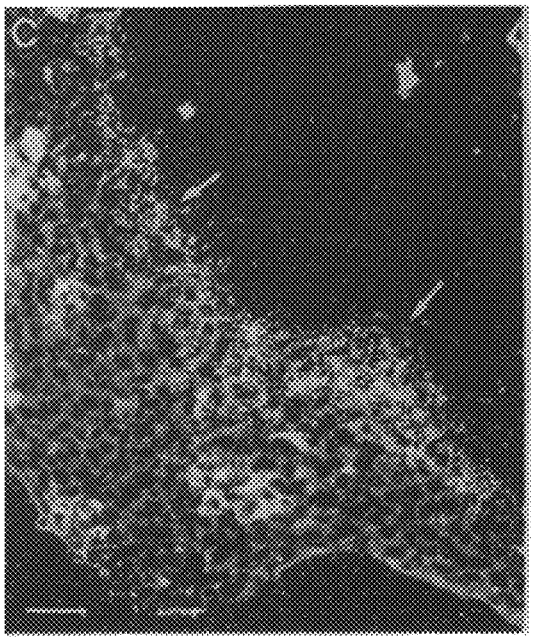
Figure 5D:
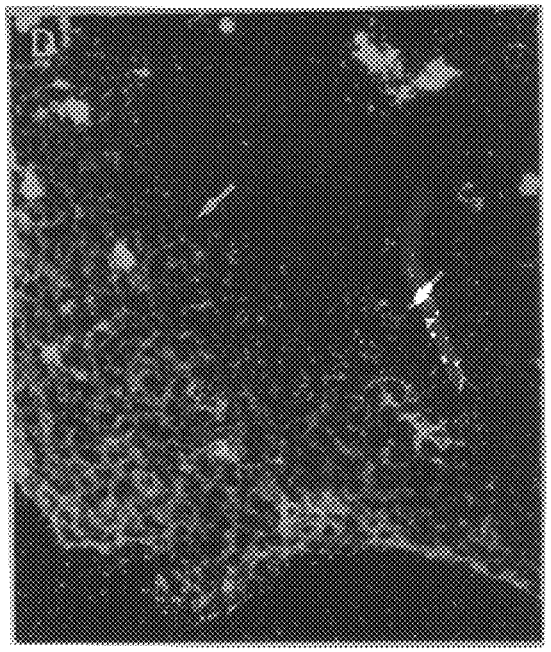
Figure 5E:
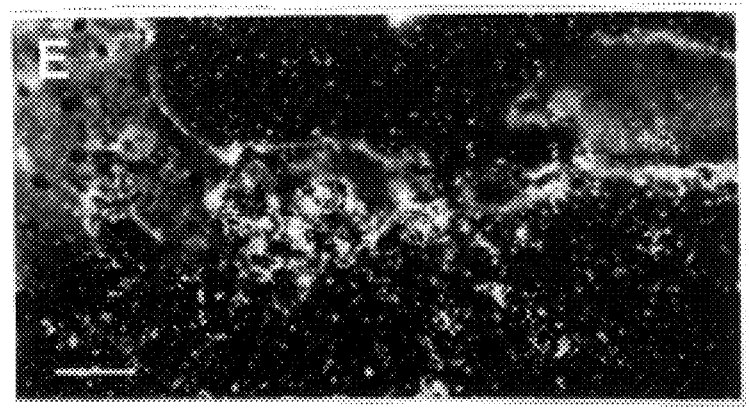
Figure 5F:
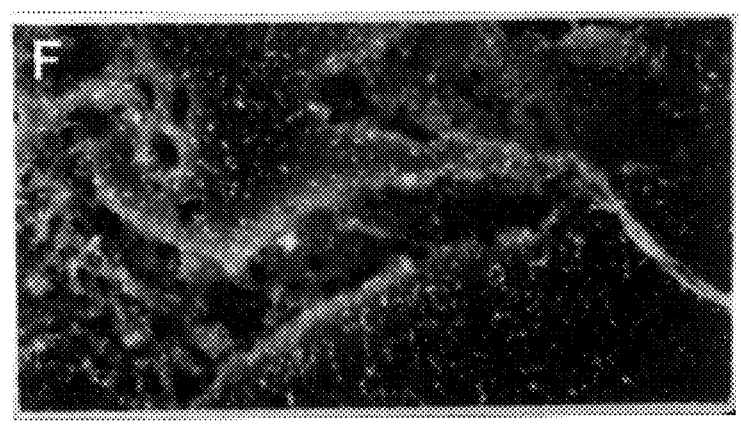

At the pre-blastema stage of regeneration there were two FGFR2-hybridizing regions observed in the regenerate, as shown in FIG. 5A. The first region was in the wound epithelium. At this stage, the wound epithelium was 5–10 cell layers thick and the hybridization was seen in the basal cells adjacent the underlying mesenchyme but not in the outer layers, as shown in FIG. 5C. This hybridization did not extend into the limb epidermis and thus was specific for the wound epithelium. Additional hybridization was also observed in the cells of the periosteum, as shown in FIG. 5E. At this stage no signal is detected over the differentiating mesenchyme cells, as showns in FIG. 5A. The hybridization signals are specific to the FGFR2, since the sense probe revealed negligible signals in the wound epithelium and periosteum, as shown in FIGS. 5B, 5D and 5F.

Figure 6A:
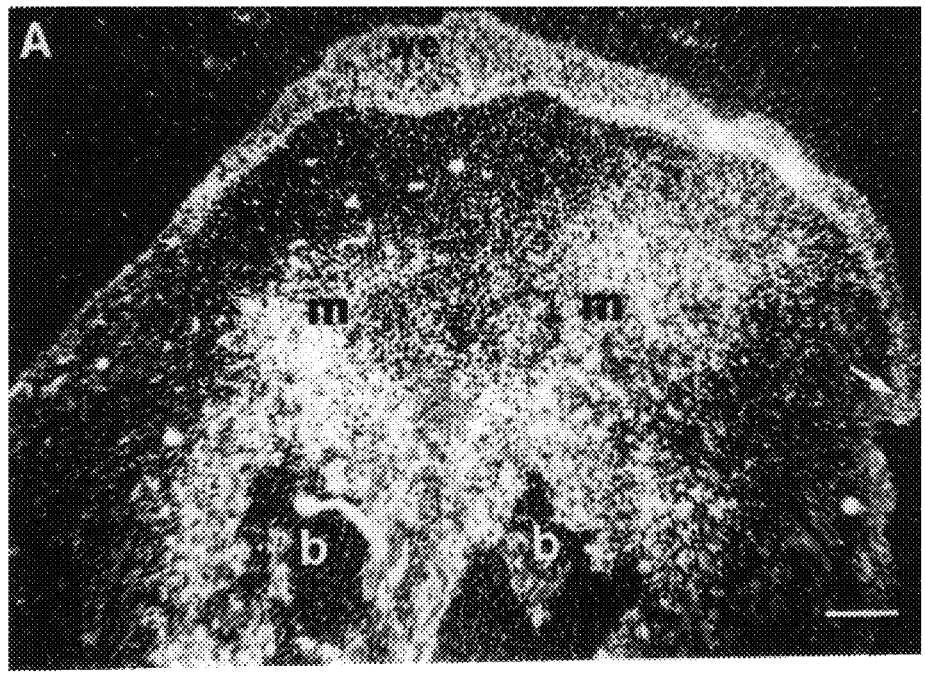
FIGS. 6A and 6B are dark-field micrographs showing the hybridization pattern of the anti-sense FGFR2 riboprobe to an early bud blastema at low (FIG. 6A) and high (FIG. 6B) magnification. The low-magnification in FIG. 6A shows FGFR2 transcripts in the cells of the basal layer of the wound epithelium (we) which decrease dramatically in the stump epidermis (white arrow marks border of wound epithelium and epidermis). FGFR2 mRNA is also seen in the mesenchymal cells (m) of the blastema closely associated with the bisected bones (b). The high-magnification of FIG. 6B shows that the FGFR2 mRNA is restricted to the wound epithelium and mesenchyme (m) and decreases abruptly at the amputation level (white arrow). Stump epidermis=e. A, Bar=180 µm; B, Bar=70 µm.
Figure 6B:
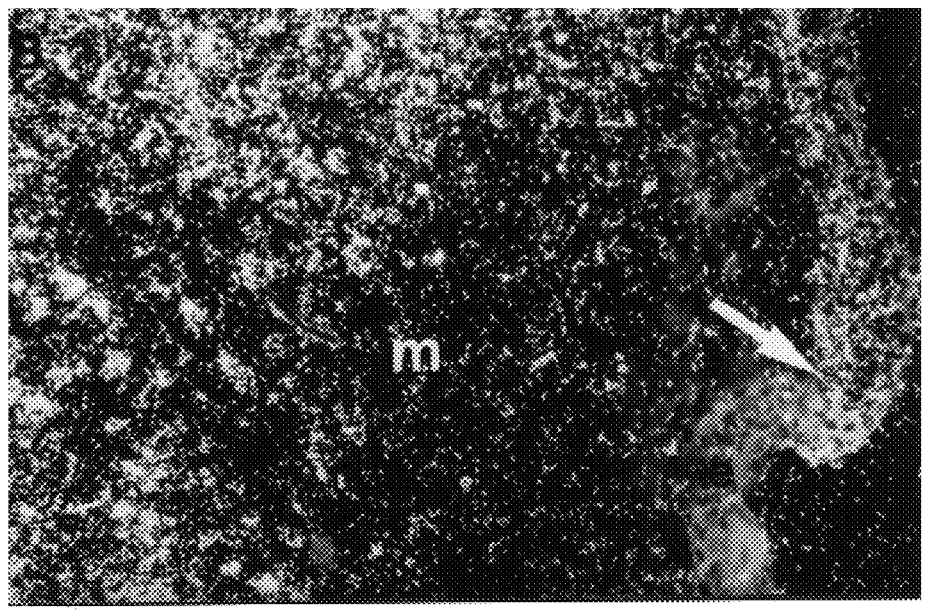

The early bud blastema showed three distinct hybridization areas. The first was the basal layer of the wound epithelium, shown in FIG. 6A, as seen in the pre-blastema stage shown in FIG. 5. At a higher magnification, it was apparent that the hybridization signal decreases abruptly at the amputation boundary, as shown in FIG. 6B. The second was in the blastema mesenchyme but was largely restricted to cells in the core of the blastema adjacent the ends of the bisected bones as shown in FIG. 6A. In contrast, little hybridization was seen in the more distal mesenchymal cells adjacent the wound epithelium. The third area of hybridization was in the periosteum, observed in the stump (FIG. 6A) as in the pre-blastema stage regenerate.

Figure 7:
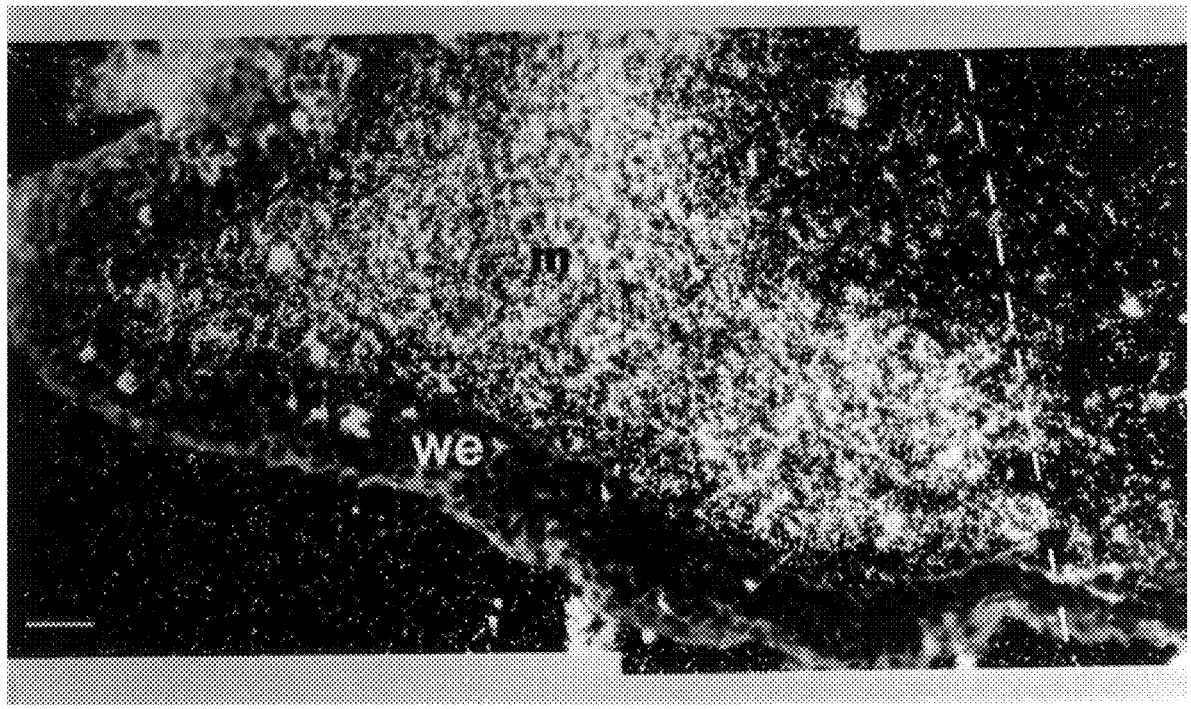
FIG. 7 is a micrograph illustrating hybridization of the FGFR1 anti-sense riboprobe in a mid bud blastema, visualized by dark-field microscopy. This micrograph shows the restricted localization of FGFR1 mRNA to the blastema mesenchyme (m) and its distinct absence from the wound epithelium (we) and stump tissue. The white dashed line indicates the level of amputation. Bar=70 µm.

The mid bud blastema showed the same pattern. of hybridization to FGFR2 as the early bud blastema but a greater intensity of signal was seen in the blastema mesenchyme, probably due in part to the increased cell number at this stage of regeneration. The hybridization signal seen in the basal cell layer of the wound epithelium remained unchanged. At this same stage, the FGFR1 hybridization pattern was restricted to the blastema mesenchyme and appeared to be homogeneously distributed throughout the blastema, as shown in FIG. 7. In contrast to the FGFR2-hybridizing pattern, there was no apparent FGFR1 hybridization in the wound epithelium as shown in FIG. 7.

Figure 8A:
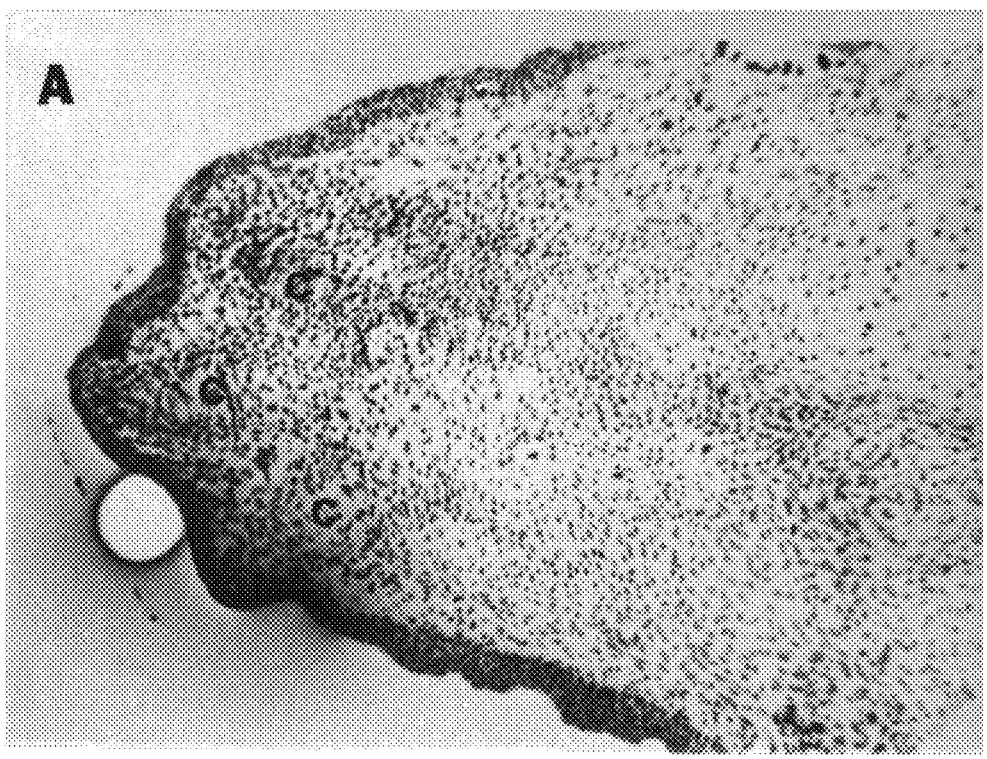
FIGS. 8A and 8B are light-field (FIG. 8A) and dark-field (FIG. 8B) micrographs of an early digit stage regenerate hybridized to the antisense FGFR2 riboprobe. The expression pattern is very specific to the cells of the condensing cartilage (c). Bar=175 µm.
Figure 8B:
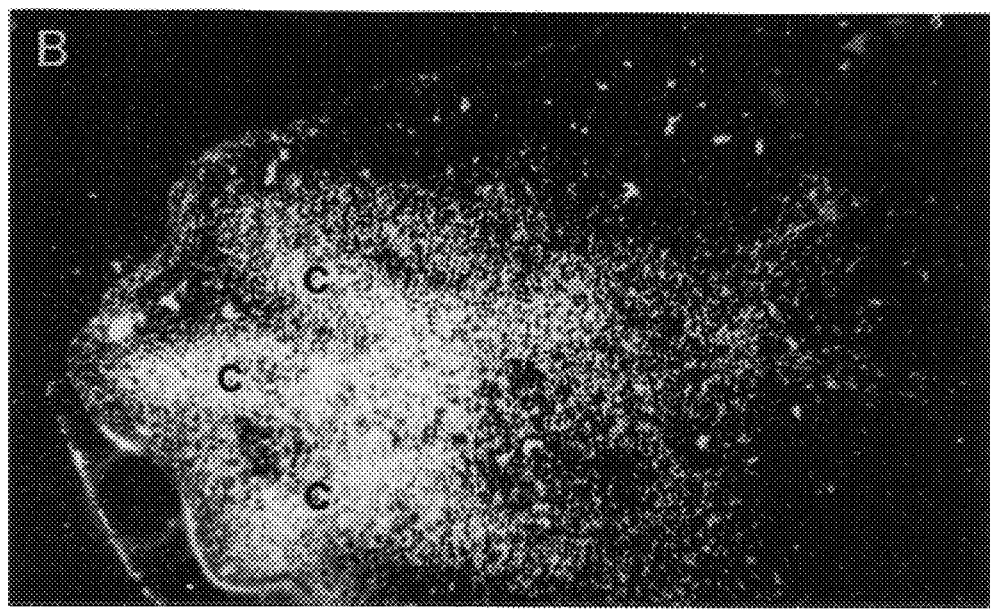
Figure 9A:
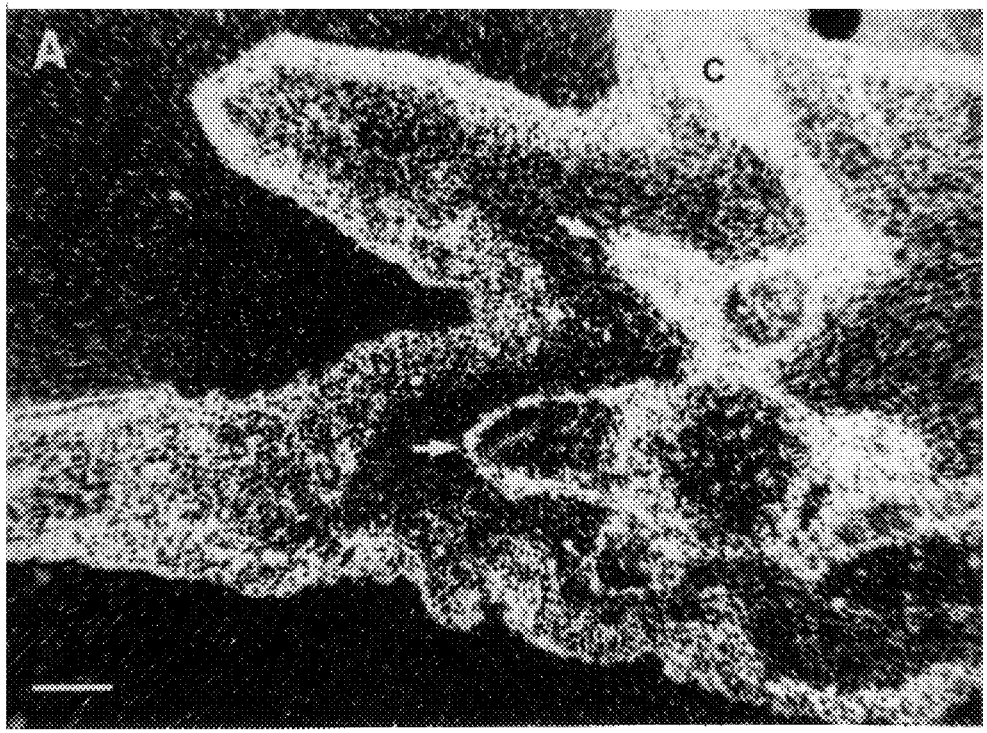
FIGS. 9A and 9B are dark-field micrographs showing the location of FGFR2 mRNA in a late digit regenerate, and the specificity of the FGFR2 riboprobe. The micrograph in FIG. 9A shows FGFR2 expression associated with the condensing cartilage (c) and the periosteum (white arrows). The micrograph in FIG. 9B is a section hybridized to the sense transcript. Bar=170 µm.
Figure 9B:

As growth slowed and differentiation began, a different pattern of hybridization to FGFR2 emerged. Hybridization was now concentrated in the condensing cartilage and followed the pattern of the forming digits. The wound epithelial expression of FGFR2 detected early in the pre-blastema stage, which lasted till the mid-bud stage, was no longer observed, as shown in FIG. 8. As differentiation continued into the digit stages of regeneration, the pattern of hybridization to FGFR2 became more restricted to the perichondrial regions of the forming digits and metacarpals, with less intense hybridization remaining in the pre-ossified cartilage of the regenerate, as shown in FIG. 9.

Figure 10:
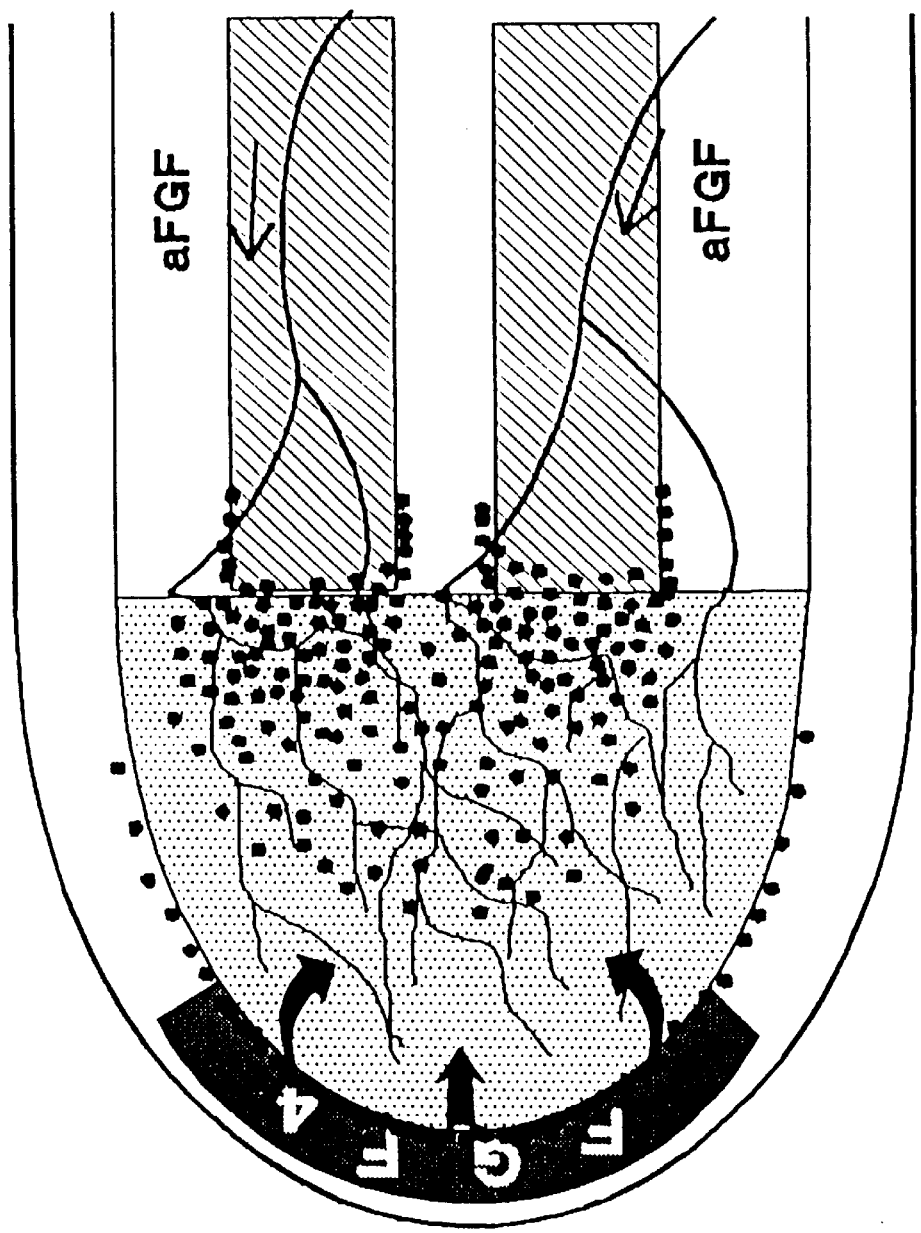
FIG. 10 is a diagram showing the interactions of FGFs and their receptors in regenerating limbs. FGFR1 is expressed by all blastema mesenchyme cells (light grey). FGFR2 is expressed by cells of the cartilage lineage and by basal cells of the wound epithelium (circles). Neurons synthesize aFGF which is transported by axons (thick lines) to blastema (as indicated by thin arrows) where it interacts with FGFR1 or FGFR2 on mesenchyme cells to stimulate their division. FGF-4 is produced by wound epithelium (dark grey) which also interacts with FGFR1 on mesenchyme cells (as indicated by thick arrows) to further stimulate cell division and/or to prevent differentiation. One of the FGFs interacts with FGFR2 to restrict cells to the cartilage lineage and/or to cause the FGFR2 expressing cells to form cartilage. FGFR2 expressed by the wound epithelium is involved in either FGF stimulation of wound epithelial cell cycling and/or in a specific function of the wound epithelium.

The newt FGF receptors 1 and 2 (NvFGFR1 and NvFGFR2) are both expressed in the blastema during forelimb regeneration. However, the temporal and spatial expression patterns of these receptors are different, indicating that the two receptors may have different roles. FGFR1 expression is restricted to the blastema mesenchyme and appears to be homogeneously distributed throughout the blastema. FGFR2 is expressed in the core of the blastema adjacent and surrounding the bisected bone, as well as in the basal layer of cells in the wound epithelium during the stages of regeneration associated with growth and blastema cell proliferation. During differentiation stages, FGFR2 expression is predominantly seen in the condensing cartilage of the early digit stage and in the perichondrium of the late digit stage. FGFR1 is a receptor for aFGF, bFGF and FGF-4;

FGFR2 is a receptor for aFGF and either bFGF or KGF, depending on the isoform. Thus, it is now believed that blastema cells respond to different FGF ligands. The cellular source of various members of the FGF growth factor family is shown in FIG. 10 which describes a testable model to account for a multiplicity of FGF's and FGFR's in regenerating limbs. This model is established based on the in situ hybridization results disclosed herein for the FGFRs shown here and on other results for the FGFs.

The relative levels of receptor mRNAs in the different newt tissues are also different as shown by Northern analyses. FGFR1 is expressed at higher levels in the mesodermally derived kidney and liver than in the neutrally derived brain and eye. There is no expression of this receptor in the spleen. FGFR2, on the other hand, is expressed at higher levels in the brain and eye than in the kidney and liver and expression is detectable in the spleen. FGFR1 expression seems to correlate strongly with mesodermal tissues as seen in the kidney and liver by Northern hybridization, as shown in FIG. 4, and in the blastema mesenchyme observed by in situ hybridization, as shown in FIG. 7. FGFR2, on the other had, is shown to be expressed at high levels in nervous tissue by Northern hybridization. It is now believed that the expression of FGFR2 in the blastema, as seen by in situ hybridization, is in response to the neurotrophic factor(s) released into the blastema by nerves in developing mouse limbs, FGF-4 is expressed in the apical ectodermal ridge (AER) and, since FGF-4 has a signal peptide and can therefore be secreted, it was suggested that the target of FGF-4 is the limb mesenchyme (Niswander et al, 1992, supra). It is likely that the AER and the wound epithelium carry out similar functions, i.e., epithelial/mesenchymal interactions, essential for limb bud development and blastema outgrowth, respectively (Muneoka et al., 1992, Molecular aspects of regeneration in developing vertebrate limbs, *Dev. Bio.* 152:37–49). Thus, the wound epithelium may also release FGF-4 into the mesenchyme where it interacts with FGFR1 and stimulates mesenchyme growth, as shown in FIG. 10. Another possible source of one or more FGFs is the nerve. Nerves are essential for limb regeneration (Singer, 1952, The influence of the nerve in regeneration of the amphibian extremity. *O. Rev. Biol.* 27:169–200) but the identity of the putative neurotrophic factor(s) is not yet known (Carlone et al., 1985, Trophic factors from nerves. *Regulation of Vertebrate Limb Regeneration*, (ed. R. E. Sicard), pp. 93–105. Oxford University Press, New York). it has been shown that a crude FGF preparation exhibited some mitogenicity when infused into denervated newt limb stumps (Mescher et al, 1979, supra; Gospodarowicz et al., 1980, supra). in mice, it was shown that aFGF mRNA is present in ganglia by in situ hybridization and that aFGF is present within peripheral nerves closely associated with the cytoplasmic side of the axonal membranes by immunohistochemical studies (Elde et al., 1991, Prominent expression of acidic fibroblast growth factor in motor and sensory neurons. *Neuron* 7:349–364). Moreover, aFGF is present in the blastema during limb regeneration in axolotis (Boilly et al., 1991, supra). Thus, it is possible that during blastema development aFGF is released from nerves into the blastema where it can react with mesenchymal cells expressing FGFR1, and with the cells that are expressing FGFR2 in the core of the blastema adjacent the bisected bone. It may also interact with the cells within the wound epithelium that are expressing FGFR2 (FIG. 10). A recent demonstration of multiple tissue-specific promoters in the aFGF gene (Myers et al, 1993, Gene structure and differential expression of acidic fibroblast growth factor mRNA: identification and distribution of four different transcripts. *Oncogene* 8:341–349) lends credence to the theory that the aFGF gene may be equipped with the flexibility to respond to various developmental or traumatic situations.

The expression pattern of FGFR2 raises the possibility that this receptor is restricted to the cartilage lineage. The expression of FGFR2 in the blastema is seen initially in those cells closely associated with the bisected ends of the radius and ulna. Subsequently, FGFR2 expression is associated with mesenchymal cells condensing to form the skeletal promordia. Utilizing triploidy and thymidine-labeled grafts of either cartilage or muscle, Steen, 1968, Stability of chondrocyte differentiation and contribution of muscle to cartilage during limb regeneration in the axolotl (*Siredon mexicanum*). *J. Exp. Zool.* 167:49–78), showed that in axolotis, the cartilage lineage is very stable; most cartilage cells give rise to blastema cells that then redifferentiate back into cartilage. It has also been shown that connective tissue cells can give rise to cartilage (reviewed in Bryant et al., 1992, Retinoic acid, local cell-cell interactions and pattern formation in vertebrate limbs. *Dev. Biol* 152:1–25). While lineage studies have not been done in newts, the inventors believe that periosteal cells contribute to the blastema cartilage lineage. This view is supported by the inventors' observation in unamputated limbs (data not shown) and in the limb stump (FIG. 5E) that FGFR2 is expressed in periosteal cells and in cartilage of the epiphyses of the radius and ulna and in the autopodium. Thus, chondrocytes and periosteal cells already expressing FGFR2 may be recruited into the blastema early in regeneration and then largely maintained in the cartilage lineage. In this regard, Gospodarowitz et al., 1980, supra, showed that FGF preparations can stimulate chondroblast proliferation. Also, aFGF has been isolated from bovine scapular cartilage (Sullivan et al., 1985, Purification of cartilage-derviced growth factor by heparin affinity chromatography. *J. Biol. Chem.* 260:2399–2403) and bone (Hauschka et al., 1986, Growth factors in bone matrix. Isolation of multiple types by affinity chromatography on heparin sepharose. *J. Biol. Chem.* 261:12665–12674). Perhaps in regeneration, aFGF interacts with FGFR2 to stimulate chondroblast proliferation and/or to maintain the cartilage lineage.

The results shown herein suggest that FGFR2 also play a role in specific functions of the wound epithelium and/or in wound epithelial development into skin. It is shown herein that FGFR2 expression is observed in the basal layer of the wound epithelium during pre-blastema stages and this expression persists until differentiation stages. In the developing mouse, the entire body ectoderm, including the limb bud ectoderm, expresses FGFR2 (Orr-Urtreger et al., 1991, supra; Peters et al., 1992, supra) suggesting that FGFR2 is important for normal development of skin. In a wound healing study, KGF was shown to be induced 160 fold one day after skin injury (Werner et al., 1992, supra). This large induction was unique within the FGF family, since mRNA levels of aFGF, bFGF and FGF-5 were induced only 2- to 10-fold during wound healing, and there was no expression of FGF-3, FGF-4 and FGF-6 detected in normal and wounded skin. In situ hybridization showed expression of KGF in the dermis while FGFR2 was predominatly expressed in the epidermis (Werner et al., 1992, supra). The spatial and temporal patterns of expression of FGFR1 and FGFR2 (FIGS. 5–9) during limb regeneration are reminiscent of those seen in embryonic limb development (Orr-Urtreger et al., 1991, supra; Peters et al., 1992, supra). Furthermore, at the initial stage of blastema formation, the distribution of the FGF receptors in the wound epithelium duplicate those seen in the back skin wounding model (Werner et al., 1992, supra).

The wound epithelium is a necessary component of the regenerate (Singer et al, 1961, supra) and has been shown to express a number of molecules not expressed by skin epidermis, including the antigens designated WE3 (Tassava et al., 1986, Regenerate epithelium and skin glands of the adult newt react to the same monoclonal antibody. *J. Exp. Zool.* 239:229–240), WE4 (Castilla et al., 1992, Extraction of the WE3 antigen and comparison of reactivities of mAbs WE3 and WE4 in adult newt regeneration epithelium and body tissues. In *Keys for Regeneration*, (ed. C. H. Taban and B. Boilly), vol. 23, pp. 116–130. Karger, Basel.), MT1/tenascin (Onda et al., 1991, Characterization of a newt tenasin cDNA and localization of the tenascin mRNA during newt limb regeneration by in situ hybridization. *Dev. Biol* 148:219–232), and MT2 (Klatt et al., 1992, Monoclonal antibody MT2 identifies an extracellular matrix glycoprotein that is co-localized with tenascin during adult newt limb regeneration. *Differentiation* 50:133–140). The interaction of FGFR2 with its ligand is involved with the synthesis and/or function of these wound epithelial antigens. Finally, while innervation of the wound epithelium is not essential for regeneration (Sidman et al., 1960, Limb regeneration without innervation of the apical epidermis in the adult newt, Triturus. *J. Exp. Zool.* 144:105–110, an FGF-like neurotrophic factor released from nerves may nevertheless interact with FGFR2 in the wound epithelium, either in stimulating proliferation or in establishing a functional wound epithelium. Thus, the results herein show that heterogeneity exists in the expression patterns of FGFR1 and FGFR2 during limb regeneration in newts.

This invention will now be illustrated by the following examples. Adult newts, *Notophthalmus viridescens*, were collected in southern Ohio, maintained in aged tap water at room temperature, and fed raw beef liver four times a week. Limbs were amputated through the midradius/ulna and protruding bones were trimmed to the level of soft tissues. Newts were then returned to water and allowed to regenerate to the desired stage. Regenerates were collected at 5 and 10 days after amputation (preblastema stages), and at early-bud, mid-bud, late-bud, palette and digit stages (staged according to Iten et al., 1973, supra). From two to six limbs/regenerates were sampled at each stage. Operations were performed while animals were anesthetized with MS-222 (ethylm-aminobenzoate methanesulfonate; Sigma, St. Louis, Mo.). Cloning and Sequencing of Newt FGFR1 and FGFR2

A 2.0 kbp EcoRI fragment from a human FGFR1 /flg cDNA clone (Ruta et al., 1988, A novel protein tyrosine kinase gene whose expression is modulated during endothelial cell differentiation. *Oncogene* 3:9–16), was used to screen a newt mid-bud blastema cDNA library constructed in λgt11 (Ragsdale et al., 1989, Identification of a novel retinoic acid receptor in regenerative tissues of the newt. *Nature* 341:654–657). A total of $5 \times 10^5$ plaques ($5 \times 10^4$ plaques/150 mm plate) were transferred to duplicate nitrocellulose filters (Schleicher & Schuell) and hybridized to a random primed human FGFR1 cDNA probe under low stringency (43% formamide, 5×SSC, 5×Denhardt's solution, 1% SDS, 200 μg/ml salmon sperm DNA in 50 mM phosphate buffer, pH 6.5 at 37° C.). Hybridized filters were washed for 1 hr at 37° C. in 2×SSC/0.1% SDS and exposed to Kodak X-OMAT AR film overnight. The EcoRI phage inserts from isolates 102, 108 and 109 were subcloned into the EcoRI site of pBluescript KS(+) (Stratagene) or subcloned directly into the EcoRI site of pBR322 derived from the *E. coli* strain Y1088 (Chiu et al., 1992, Cloning of complementary DNA inserts from phage DNA directly into plasmid vector. *Methods Enzymol.* 216:508–516) for DNA sequence analysis. One of the two EcoRI sites of phage clone 110 was missing and the insert cDNA could not be excised by EcoRI digestion. Therefore, primers flanking the phage EcoRI cloning site were used in polymerase chain reactions (PCR) to amplify the phage insert. A single band was isolated and cloned into the HindII site of pBluescript KS(+). Rescreening of the cDNA library was carried out under high stringency using the 240 bp EcoRI-BamHI fragment of Clone 109 as a probe. Nested deletions of the phage clones 102, 109, 110 and 310 were generated in both orientations using the method of Henikoff, 1984, Unidirectional digestion with exonuclease III creates targeted breakpoints for DNA sequencing. *Gene* 28:351–359). Double and single-stranded DNA from selected clones were sequenced using the dideoxy method (Sanger, 1977, DNA sequencing with chain-terminating inhibitors. *Proc. Natl. Acad. Sci. USA* 74:5463–5467) and Sequenase (USB).
RNA Isolation and Northern Hybridization RNA was isolated from frozen tissues by acid guanidinium isothiocyanate extraction followed by CsCI gradient centrifugation (Chirgwin et al., 1979, Isolation of biologically active ribonucleic acid from sources enriched in ribonucleases. *Biochemistry* 18:5294–5299. RNA samples were electrophoresed through 1.0% agarose/formamide gels, transferred to Hybond-N nylon membrances and probed with anti-sense [$\alpha$-$^{32}$P]UTP-labled riboprobes. The filters were washed twice in 2×SSC/0.1% SDS for 15 min at 65° C. and twice in 0.1×SSC/0.1% SDS for 15 min at 65° C. The membranes were then exposed to Kodak X-OMAT AR film and developed.

In Situ Hybridizations To generate FGFR2 specific riboprobes, a 306 bp BbsI-BamHI fragment from Clone 310 was subcloned into the SmaI site of pBluescript SK(+) and designated MP70-1. To generate an antisense transcript, 1 μg of MP70-1 was digested with EcoRI and in vitro transcription was carried out using T3 RNA polymerase according to the manufacturer's protocol (Stratagene). The sense strand transcript was generated by digestion of MP70-1 with BamHl followed by in vitro transcription using T7 RNA polymerase. FGFR1 specific riboprobes were generated using the exonuclease III/mung bean nuclease generated deletion clones used in the sequencing reactions (see above) that allowed the synthesis of the sense and anti-sense transcripts representing the 73 amino acid carboxy terminal tail of the receptor and 80 nucleotides of the 3'-untranslated sequence. All transcription reactions were performed in the presence of [$^{35}$S]UTPαS. The RNA probes were purified by Nuctrap push columns (Stratagene).

Blastemas with a small amount of stump tissue were isolated and fixed in 4% paraformaldehyde containing 1×PBS, pH 7.2, for 2 hr at 4° C. The blastemas were then washed two times in 1×PBS at 4° C. for 30 min, and frozen on a dry ice/isopropanol slurry in OCT compound. Ten μm cryosections were placed on TESPA (3-triethoxysilylpropylaminle) treated slides and fixed for 20 min in 4% paraformaldehyde containing 1×PBS. The slides were dehydrated through graded ethanol and stored at −80° C. until hybridization. Prior to hybridization the sections were treated with proteinase K (20 μg/ml) for 10 min at 37° C., acetylated by immersing slides in 0.25% acetic anhydride in 0.1M triethanolamine buffer, pH 8.0 for 20 min and dehydrated through graded ethanol solutions. The hybridizations were carried out at 50–55° C. in hybridization mix (50% formamide, 0.3M NaCl, 10 mM Tris-HCl, 1×Denhardt's solution, 5 mM EDTA, 0.5 mg/ml yeast tRNA, 10% dextran sulfate, pH 7.5) with either sense or antisense riboprobes at a concentration of 1×10⁷ cpm/ml for 16 hr.

Slides were washed in 4×SSc for 5 min at room temperature before a 30 min wash in 50% formamide/2×SSC/0.1% 2-mercaptoethanol at 50–55° C. The slides were then treated with RNase A (20 μg/ml) for 30 min at 37° C. The slides were further washed in 50% formamide/2×SSC/0.1% 2-mercaptoethanol for 30 min at 50–55° C., 2× and 0.1×SSC each for 15 min at 50–55° C. The sections were then dehydrated, coated with Kodak NTB-2 emulsion diluted 1:1 with distilled water and exposed for 15 to 20 days. Slides were developed with Kodak D-19 developer for 2.5 min at 15° C. and fixed for 5 min with Kodak fixer. Sections were stained with hematoxylin and counterstained with eosin. The sections were visualized with both dark- and light-field microscopy.

The newt aFGF proteins are useful biological materials for promoting in vitro growth of cultured cell lines, such as cell lines that have been transformed by recombinant IDNA techniques to produce other useful proteins. The aFGF proteins are also useful for enhanced would healing.

Substantially pure aFGF or the non-toxic salts thereof, can be combined with a pharmaceutically acceptable carrier to form a pharmaceutical composition and may be administered to mammals in an acceptable manner such as intravenously, subcutaneously, intramuscularly or orally. It is to be understood that the required dosage will vary with the particular condition being treated, with the severity of the condition and with the duration of desired treatment. For example, such peptides can be administered in the form of pharmaceutically acceptable non-toxic salts, (i.e., acid addition salts or metal complexes, e.g., with zinc, iron or the like, which are considered as salts for purposes of this application). it is known that acid addition salts include hydrochloride, hydrobromide, sulphate, phosphate, maleate, acetate, citrate, benzoate, succinate, malate, ascorbate, tartrate and the like. According to acceptable pharmaceutical practices if the active ingredient is administered in tablet form, the tablet may contain a binder, such as tragacanth, corn starch or gelatin; a disintegrating agent, such as alginic acid; and a lubricant, such as magnesium stearate. If the active ingredient is administed in liquid form, sweetening and/or flavoring may be used. if the active ingredient is administered by intravenous injection, the active ingredient maybe delivered in isotonic saline, phosphate buffer solutions or the like.

Further, according to acceptable pharmaceutical practices the active ingredient should be administered under the guidance of knowledgeable persons. The pharmaceutical compositions will usually contain the active ingredient in conjunction with a conventional, pharmaceutically-acceptable carrier. The aFGF active ingredients may be administered in conjunction with other therapeutic agents, including other mitogens, such as platelet-derived growth factor, epidermal growth factor, insulin-like growth factors, and transforming growth factors.

C. Biochemical and Functional Characterization of Newt FGFR2

Figure 11:
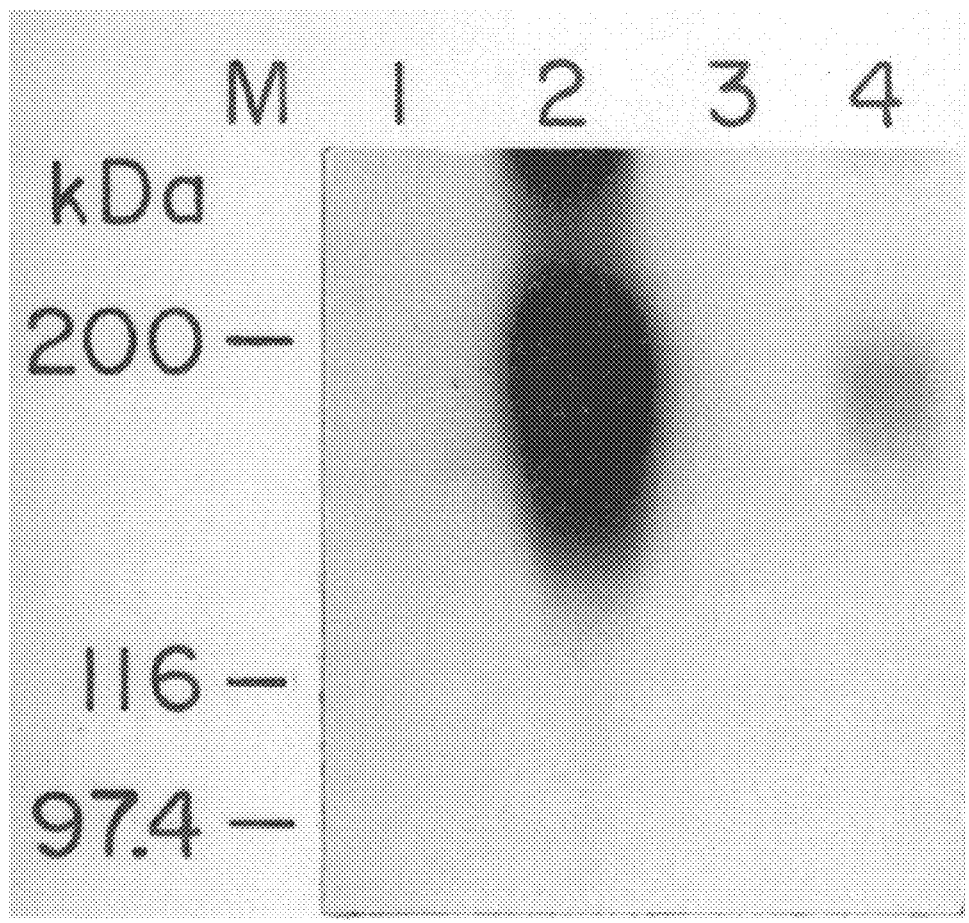
FIG. 11 shows crosslinking studies using CHO cells overexpressing newt KGFR cDNA. CHO cells transfected with pBJ5 vector (lane 1) or with newt KGFR expression vector (lanes 2–4) were crosslinked with $^{125}$I-aFGF using 0.3 mM disuccinimidyl suberate (DSS). Excess amounts (500-fold) of aFGF (lane 3) or KGF (lane 4) were used to compete with $^{125}$I-aFGF. Crosslinked products were analyzed on a 7.5% SDS-polyacrylamide gel.

To characterize the newt FGFR EDNA functionally, the newt KGFR were expressed in CHO-K1 cells. The mammalian expression vector, pBJ5, which contains a chimeric promoter derived from HTLV-I and SV40, was used to express the newt KGFR and FGFR2 cDNA. Crosslinking studies on CHO-K1 cells over-expressing the newt KGFR (KPTr2-2) showed a crosslinked product migrating at 150 kDa when using $^{125}$I-labeled bovine brain aFGF or recombinant human aFGF as the ligand. The crosslinked product can be successfully competed off with a 500-fold molar excess of cold aFGF or human recombinant KGF as shown in FIG. 11. The crosslinked product is absent in KPTr1-8, the CHO cells that were transfected with the pBJ5 vector alone. The crosslinked product thus appears to be specific. Similarly, a cell line over-expressing the human KGFR (T-1063-29-2 from S. A. Aaronson, NIH) was able to produce a somewhat smaller crosslinked product than the newt KGFR. Antibodies (both monoclonal and polyclonal) directed against a peptide from the carboxyl terminus of the newt FGFR2 are generated.

Binding assays using KPTr2-2 and $^{125}$I-aFGF have been carried out. The Scatchard plot from these assays revealed that the newt KGFR has a $K_d$ of 1.3 nM toward human aFGF and the KPTr2-2 cell line expresses about 355,500 receptors per cell. The $K_d$ is slightly higher than the typical sub-nM range of mammalian KGFR. However, this may reflect the species difference since we used a human ligand for the newt receptor. A competition assay using KPTr2-2 and $^{125}$I-aFGF showed that human recombinant bFGF does not compete as well as aFGF. This result is consistent with the observation published for human KGFR.

The CHO-K1 cell line (KPTr2-2) expressing newt KGFR has been deposited with the ATCC on May 25, 1993 and given Accession Number CRL-1 1361.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should be depository be unable to furnish a sample when requested, due to the condition of the deposit. All restrictions on the availability to the public of the subject culture deposit will be irrevocably removed upon the granting of a patent disclosing it.

D. Mutant Cell Lines that are Non-responsive to FGF

Figure 12:
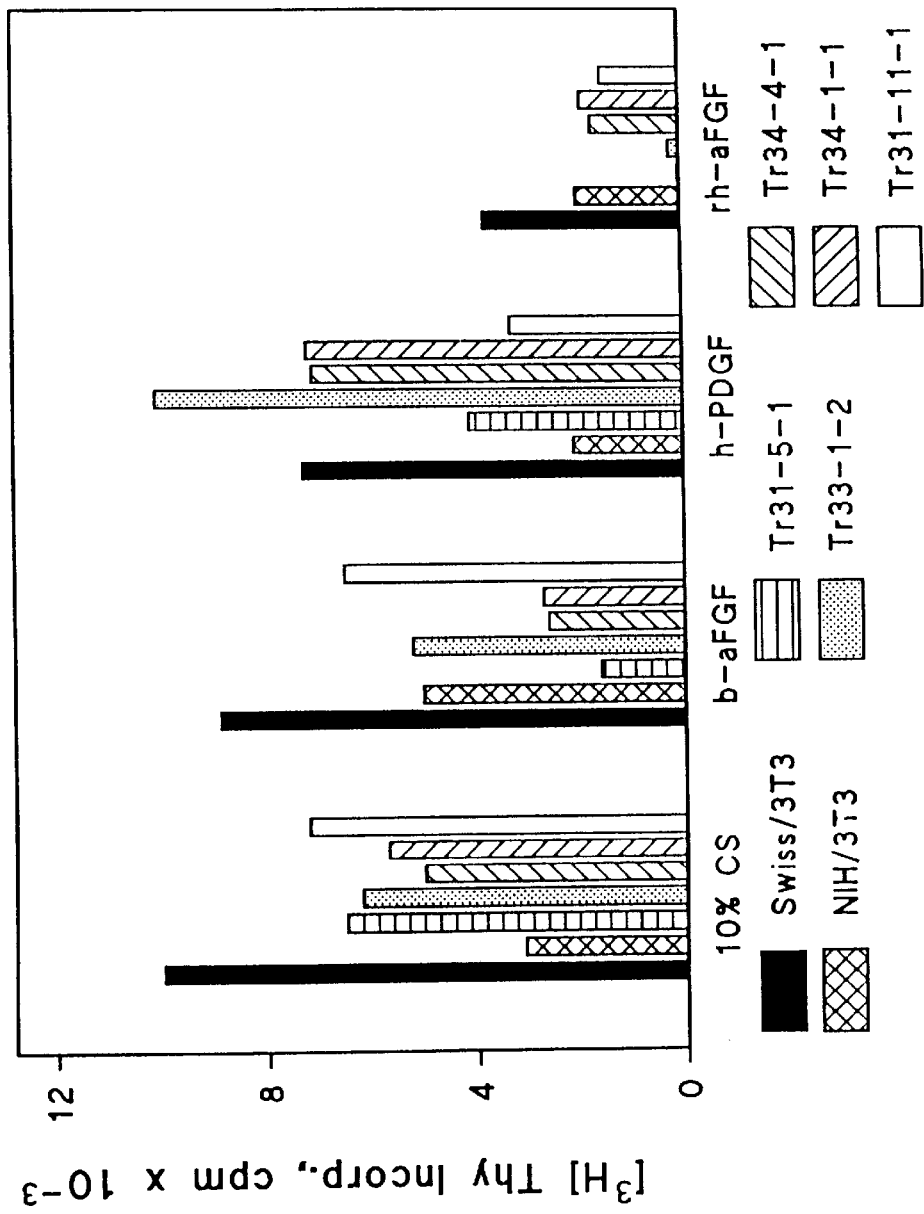
FIG. 12 is a graph showing the mitogenic effects of different growth factors to various transfected cell lines. Cells were grown to confluence, changed to Dulbecco's modified Eagle medium containing 0.5% calf serum and grown for two more days. Different growth factors or calf serum was then added to the medium to stimulate cells to grow. [$^3$H]thymidine was added 18 hours after addition of the mitogens and cells were incubated for another 6 hours. Bovine aFGF (b-aFGF) represents the truncated forms while human aFGF purified from Tr31-5-1 (rh-aFGF) represents the full-length protein. Cell lines, Tr31-5-1, 33-1-2, 34-1-1, and 34-4-1 are NIH/3T3 derivatives containing the aFGF cDNA construct in the positive orientation; whereas Tr31-11-1 contains aFGF cDNA in the anti-sense orientation.

Cells transfected with the EDNA coding for the full-length human aFGF were compared with the parental NIH/3T3 cells by determining their responses to various mitogens. The sense transfectants (Tr31-5-1, Tr33-1-2, Tr34-4-1 and Tr34-1-1) displayed stronger mitogenic responses than NIH/3T3 cells when stimulated with calf serum or PDGF consistent with their being faster-growing cells. The sense transfectants, with the exception of Tr33-1-2, respond less strongly than the parental NIH/3T3 cells to the truncated form of aFGF (b-aFGF) and to the full-length aFGF (rh-1 FGF) for which Tr31-5-1 is the source. In fact, Tr31-5-1 and Tr33-1-2 failed to give any mitogenic responses to the full-length aFGF as shown in FIG. 12. These results suggest that truncated aFGF may utilize a different signaling pathway from that of the full-length aFGF. Both Swiss/3T3 and NIH/3T3, as well as sense transfectants expressing low levels of full-length aFGF and anti-sense transfectants, responded to the mitogenic stimulation of rh-aFGF. Therefore, the lack of mitogenic response of Tr31-5-1 and Tr33-1-2 to rh-aFGF is not likely due to the trivial explanation of a defective mitogen. Thus, Tr31-5-1 and Tr33-1-2 may have lost some component of the pathway and these cell lines provide a unique means for elucidating the components responsive to the full-length aFGF.

Cell lines transfected with bFGF cDNA, which over-express bFGF, down-regulate its cognate receptor. Cell lines over-expressing full-length aFGF down-regulate its cognate receptor which is different from that used by the truncated aFGF and vice versa. Therefore, the reduction in mitogenic response of Tr31-5-1 and Tr33-1-2 to full-length aFGF is a consequence of fewer cell-surface ligand binding sites. The inventors' crosslinking data using $I^{125}$-labeled b-aFGF show that Tr31-5-1 cells have 50% less cell-surface binding to truncated aFGF than NIH/3T3 cells. These cell lines are useful for the identification of agonists and antagonists of aFGF and other FGF proteins.

Since aFGF elicits its profound responses in cells through interactions with membrane FGFR, it is important to identify domains in both the ligand and the receptors that interact with each other. These results are essential to understand the molecular basis of the multiple functions of FGF action in physiological and pathological conditions. This understanding provides the basis for the rational design of both ligand and receptor antagonists. Availability of cDNA coding for aFGF and four different aFGF receptors from the same amphibian species provides reagents useful for performing "mix and match" experiments between the human and newt receptor cDNAs, as well as between human and newt aFGF cDNAs, such that antagonists and agonists to the.receptors as derivatives of human or newt aFGF are thus identified.

Although the invention has been described with regard to its preferred embodiments, which constitute the best mode presently known to the inventors, it should be understood that various changes and modifications, as would be obvious to one having the ordinary skill in this art, may be made without departing from the scope of the invention which is set forth in the claims appended hereto.

I claim:

1. A method for differentiating biological activities among the full-length form (1–154 amino acids) and truncated forms (15–154 amino acids) of aFGF proteins and other (non-aFGF) FGF proteins comprising determining the mitogenic response of a Tr31-5-1 or Tr33-1-2 cell line and comparing the mitogenic responses of the cell lines to the different forms of aFGF proteins and non-aFGF proteins.

2. The method of claim 1 wherein the cell line is Tr31-5-1 deposited with the American Type Culture Collection under Accession No. CRL-12521.

3. The method of claim 1 wherein the cell line is Tr33-1-2 deposited with the American Type Culture Collection under Accession No. CRL-12522.

4. The method of claim 1 in which the differentiation of biological activities comprises conducting a mitogenic assay to identify agonists and antagoists of aFGF and other FGF proteins.

5. A cell line Tr31-5-1 deposited with the American Type Culture Collection under Accession No. CRL-12521.

6. A cell line Tr33-1-2 deposited with the American Type Culture Collection under Accession No. CRL-12522.

* * * * *